(12) United States Patent
Linders et al.

(10) Patent No.: US 11,771,363 B2
(45) Date of Patent: Oct. 3, 2023

(54) IPSILATERAL ULCER AND PRE-ULCER DETECTION METHOD AND APPARATUS

(71) Applicant: Podimetrics, Inc., Somerville, MA (US)

(72) Inventors: David R. Linders, Waltham, MA (US); Brian Petersen, Somerville, MA (US)

(73) Assignee: Podimetrics, Inc., Somerville, MA (US)

( * ) Notice: Subject to any disclaimer, the term of this patent is extended or adjusted under 35 U.S.C. 154(b) by 610 days.

(21) Appl. No.: 16/653,456

(22) Filed: Oct. 15, 2019

(65) Prior Publication Data

US 2020/0113510 A1  Apr. 16, 2020

Related U.S. Application Data

(60) Provisional application No. 62/752,589, filed on Oct. 30, 2018, provisional application No. 62/745,925, filed on Oct. 15, 2018.

(51) Int. Cl.
*A61B 5/01* (2006.01)
*A61B 5/00* (2006.01)
*A61B 5/107* (2006.01)

(52) U.S. Cl.
CPC .............. *A61B 5/447* (2013.01); *A61B 5/015* (2013.01); *A61B 5/70* (2013.01); *A61B 5/7275* (2013.01);
(Continued)

(58) Field of Classification Search
CPC ........... A61B 5/447; A61B 5/015; A61B 5/70; A61B 5/7275; A61B 5/7282;
(Continued)

(56) References Cited

U.S. PATENT DOCUMENTS

| 4,574,359 A | 3/1986 | Ishizaka et al. |
| 4,592,000 A | 5/1986 | Ishizaka et al. |

(Continued)

FOREIGN PATENT DOCUMENTS

| CN | 1308225 A | 8/2001 |
| CN | 201312800 Y | 9/2009 |

(Continued)

OTHER PUBLICATIONS

Najafi B, Wrobel JS, Grewal G, Menzies RA, Talal TK, Zirie M, and Armstrong DG, Plantar Temperature Response to Walking in Diabetes with and without Acute Charcot: The Charcot Activity Response Test, J of Aging Res, Jun. 25, 2012, Hindawi Pub Corp, vol. 2012, doi:10.1155/2012/140968 (Year: 2012).*

(Continued)

*Primary Examiner* — Colin T. Sakamoto
*Assistant Examiner* — James F McDonald
(74) *Attorney, Agent, or Firm* — Nutter McClennen & Fish LLC

(57) ABSTRACT

A system has a body with a base having a top surface with a receiving region to receive the bottom of a single foot. Among other things, the base may be in the form of an open or closed platform with a plurality of temperature sensors in communication with the top surface of the receiving region. The plurality of temperature sensors are within the receiving region and configured to activate after receipt of a stimulus applied to one or both the platform and the plurality of temperature sensors. A comparator is configured to form a temperature range as a function of the temperature value distribution and compare a percentage of the range size of the temperature distribution to a threshold value. An output produces ulcer information indicating the emergence of an ulcer or pre-ulcer when the percentage of the range size equals or exceeds the threshold value.

12 Claims, 10 Drawing Sheets

(52) U.S. Cl.
CPC .......... *A61B 5/7282* (2013.01); *A61B 5/0008* (2013.01); *A61B 5/0075* (2013.01); *A61B 5/1074* (2013.01); *A61B 2560/0252* (2013.01); *A61B 2562/0271* (2013.01)

(58) Field of Classification Search
CPC ................ A61B 5/0008; A61B 5/0075; A61B 2560/0252; A61B 2562/0271; A61B 5/4842; G16H 50/30
See application file for complete search history.

(56) References Cited

U.S. PATENT DOCUMENTS

| | | |
|---|---|---|
| 4,629,336 A | 12/1986 | Ishizaka |
| 4,647,918 A | 3/1987 | Goforth |
| 4,648,055 A | 3/1987 | Ishizaka et al. |
| 4,669,472 A | 6/1987 | Eisenmenger |
| 4,843,577 A | 6/1989 | Muramoto |
| 4,866,621 A | 9/1989 | Ono |
| 4,878,184 A | 10/1989 | Okada et al. |
| 5,011,294 A | 4/1991 | Yamaguchi |
| 5,015,102 A | 5/1991 | Yamaguchi |
| 5,066,141 A | 11/1991 | Ikeda et al. |
| 5,070,932 A | 12/1991 | Vlasak |
| 5,259,389 A | 11/1993 | Muramoto et al. |
| 5,352,039 A | 10/1994 | Barral et al. |
| 5,473,629 A | 12/1995 | Muramoto |
| 5,642,096 A | 6/1997 | Leyerer et al. |
| 5,678,566 A | 10/1997 | Dribbon |
| 5,929,332 A | 7/1999 | Brown |
| 6,090,050 A | 7/2000 | Constantinides |
| 6,195,921 B1 | 3/2001 | Truong |
| 6,398,740 B1 | 6/2002 | Lavery et al. |
| 6,631,287 B2 | 10/2003 | Newman et al. |
| 6,767,330 B2 | 7/2004 | Lavery et al. |
| 6,807,869 B2 | 10/2004 | Farringdon et al. |
| 6,963,772 B2 | 11/2005 | Bloom et al. |
| 7,052,472 B1 | 5/2006 | Miller et al. |
| 7,167,734 B2 | 1/2007 | Khalil et al. |
| 7,206,718 B2 | 4/2007 | Cavanagh et al. |
| 7,318,004 B2 | 1/2008 | Butterfield |
| 7,637,657 B2 | 12/2009 | Yamamoto et al. |
| 7,716,005 B2 | 5/2010 | Shoureshi et al. |
| 7,726,206 B2 | 6/2010 | Terrafranca, Jr. et al. |
| 7,758,523 B2 | 7/2010 | Collings et al. |
| 8,360,987 B2 | 1/2013 | Kantro et al. |
| 9,095,305 B2 | 8/2015 | Engler et al. |
| 9,259,178 B2 | 2/2016 | Bloom et al. |
| 9,271,672 B2 | 3/2016 | Linders et al. |
| 9,326,723 B2 | 5/2016 | Petersen et al. |
| 2002/0082486 A1 | 6/2002 | Lavery et al. |
| 2006/0021261 A1 | 2/2006 | Face |
| 2006/0030783 A1 | 2/2006 | Tsai et al. |
| 2007/0038273 A1 | 2/2007 | Bales et al. |
| 2007/0039211 A1 | 2/2007 | Pichler |
| 2007/0043408 A1 | 2/2007 | Winnett et al. |
| 2008/0109183 A1 | 5/2008 | Shoureshi et al. |
| 2008/0214962 A1 | 9/2008 | Kantro et al. |
| 2008/0234943 A1* | 9/2008 | Ray .................... G16H 50/20 600/300 |
| 2009/0219972 A1 | 9/2009 | Carlsson et al. |
| 2009/0306801 A1 | 12/2009 | Sivak et al. |
| 2010/0004566 A1 | 1/2010 | Son et al. |
| 2010/0041998 A1 | 2/2010 | Postel |
| 2010/0198022 A1 | 8/2010 | Vuillerme et al. |
| 2010/0268111 A1 | 10/2010 | Drinan et al. |
| 2010/0324455 A1 | 12/2010 | Rangel et al. |
| 2011/0015498 A1 | 1/2011 | Mestrovic et al. |
| 2011/0214501 A1 | 9/2011 | Ross et al. |
| 2011/0275956 A1 | 11/2011 | Son et al. |
| 2011/0313314 A1 | 12/2011 | Gefen |
| 2012/0109013 A1 | 5/2012 | Everett et al. |
| 2012/0190989 A1 | 7/2012 | Kaiser et al. |
| 2012/0221286 A1 | 8/2012 | Bisch et al. |
| 2013/0019503 A1 | 1/2013 | Vogt |
| 2013/0211281 A1 | 8/2013 | Ross et al. |
| 2013/0261494 A1 | 10/2013 | Bloom et al. |
| 2015/0057562 A1 | 2/2015 | Linders et al. |
| 2015/0359457 A1 | 12/2015 | Blumenthal et al. |
| 2016/0100790 A1 | 4/2016 | Cantu et al. |
| 2016/0192844 A1 | 7/2016 | Linders et al. |
| 2016/0256056 A1 | 9/2016 | Petersen et al. |
| 2017/0127999 A1 | 5/2017 | Linders et al. |
| 2018/0014734 A1 | 1/2018 | Rogers et al. |
| 2018/0144815 A1* | 5/2018 | Chapman-McQuiston ................ G16H 50/30 |

FOREIGN PATENT DOCUMENTS

| | | | |
|---|---|---|---|
| CN | 202263087 U | 6/2012 | |
| DE | 20 2010 013176 U1 | 2/2011 | |
| DE | 202014105408 U1 | 11/2014 | |
| EP | 885587 A1 | 12/1998 | |
| EP | 1511419 B1 | 8/2008 | |
| JP | S55071919 A | 5/1980 | |
| JP | H03-275039 A | 12/1991 | |
| JP | 2002-269231 A | 9/2002 | |
| JP | 2004-528085 A | 9/2004 | |
| JP | 2005-533543 A | 11/2005 | |
| JP | 2009-539454 A | 11/2009 | |
| KR | 101027367 B1 | 4/2011 | |
| NZ | 514340 A * | 1/2004 | ............ G01N 25/72 |
| RU | 2433783 C2 | 11/2011 | |
| WO | 2007114768 A1 | 10/2007 | |
| WO | 2008058051 A2 | 5/2008 | |
| WO | 2009005373 A1 | 1/2009 | |
| WO | 2010021932 A2 | 2/2010 | |
| WO | 2012051394 A1 | 4/2012 | |
| WO | 2012084814 A1 | 6/2012 | |
| WO | 2015143218 A1 | 9/2015 | |
| WO | WO-2018175787 A1 * | 9/2018 | ............... A61B 5/00 |

OTHER PUBLICATIONS

Cavalheiro, A., et al., Thermographic Analysis and Autonomic Response in the Hands of Patients with Leprosy, An Bras Dermatol, 2016, 274-283, 10 pages.

Evans, A.L., et al.,"Thermography in Lower Limb Arterial Disease," Clin. Radiol. (1976) vol. 27, 6 pages.

Gatt, A., et al., "The Application of Medical Thermography to Discriminate Neuroischemic Toe Ulceration in the Diabetic Foot," The International Journal of Lower Extremity Wounds, 2018, 4 pages.

Gatt, A., et al., "The Identification of Higher Forefoot Temperatures Associated with Peripheral Arterial Disease in Type 2 Diabetes Mellitus as Detected by Thermography," Primary Care Diabetes, 2018, 7 pages.

Hauer, J., "Hand Skin Blood Flow in Diabetic Patients With Automatic Neuropathy and Microangiopathy," Diabetes Care, vol. 14, No. 10, Oct. 1991, 6 pages.

Ilo, A., et al., "Infrared Thermography and Vascular Disorders in Diabetic Feet," Journal of Diabetes Science and Technology, 2019, 9 pages.

Ilo, A., et al., "Infrared Thermography and Vascular Disorders in Diabetic Feet," Journal of Diabetes Science and Technology, 2020, vol. 14, 9 pages.

International Search Report and Written Opinion for International Application No. PCT/US2021/012698 dated Apr. 2, 2021, 19 pages.

Lin, P, et al., "Assessment of Lower Extremity Ischemia Using Smartphone Thermographic Imaging", Journal of Vascular Surgery Cases and Innovative Techniques, Dec. 2017, 4 pages.

McLoughlin, G., et al., "Thermography in the Diagnosis of Occlusive Vascular Disease of the Lower Limb," Brit. J. Surg., Aug. 1973, vol. 60, No. 8, 2 pages.

Park, E., et al., "Comparison of Sympathetic Skin Response and Digital Infrared Thermographic Imaging in Peripheral Neuropathy," Yonsei Medical Journal, vol. 35, No. 4, 1994, 9 pages.

Peleki, A., et al., "Novel Use of Smartphone-based Infrared Imaging in the Detection of Acute Limb Ischaemia," EJVES Short Reports (2016) 32, 3 pages.

(56) References Cited

OTHER PUBLICATIONS

Sagaidachnyi, A., et al., "Thermography-based Blood Flow Imaging in Human Skin of the Hands and Feet: A Spectrum Filtering Approach," Institute of Physics and Engineering in Medicine, Physiol Meas. 38 (2017), 18 pages.
Schmidt, B., et al., "Describing Normative Foot Temperatures in Patients With Diabetes-Related Peripheral Neuropathy," Journal of Diabetes Science and Technology 2020, vol. 14, 6 pages.
Sebastian, A. et al., "Clinical Features, Radiological Characteristics and Offloading Modalities in Stage0 Acute Charcot's Neuroarthropathy—A Single Centre Experience from South India," Diabetes & Metabolic Syndrome: Clinical Research & Review, 13 (2019), 5 pages.
Staffa, E., "Infrared Thermography as Option for Evaluating the Treatment Effect of Percutaneous Transluminal Angioplasty by Patients with Peripheral Arterial Disease," Vascular Online, first published on Mar. 17, 2016, 8 pages.
Wallace, G., et al., "The Use of Smart Phone Thermal Imaging for Assessment of Peripheral Perfusion in Vascular Patients" Annals of Vascular Surgery (accepted manuscript) 2017, 18 pages.
Bagavathiappan, S., et al., "Correlation between Plantar Foot Temperature and Diabetic Neuropathy: A Case Study by Using an Infrared Thermal Imaging Technique," Journal of Diabetes Science and Technology, vol. 4, Issue 6, Nov. 2010, 7 pages.
Balbinot, L., et al., "Plantar Thermography is Useful in the Early Diagnosis of Diabetic Neuropathy," 2012 CLINICS, pp. 1419-1425, 7 pages.
Balbinot, L., et al., "Repeatability of Infrared Plantar Thermography in Diabetes Patients: A Pilot Study," Journal of Diabetes Science Technology, vol. 7, Issue 5, Sep. 2013, pp. 1130-1137, 9 pages.
Ammer et al. Thermal Imaging of Skin Changes on the Feet of Type II Diabetics, 2001 Conference Proceedings of the 23rd Annual International Conference of the IEEE Engineering in Medicine and Biology Society, Istanbul, Turkey, Oct. 25-28, 2001, 4 pages.
Armstrong et al. Monitoring Healing of Acute Charcot's Arthropathy with Infrared Dermal Thermometry, Journal of Rehabilitation Research and Development, vol. 34, No. 3, Jul. 1997, pp. 317-321.
Brioschi et al. "Automated Computer Diagnosis of IR Medical Imaging," FLIR Technical Series, Application Note for Research & Science, FLIR Systems, Inc., 2011.
Caselli, M.D. et al. "The Forefoot-to-Rearfoot Plantar Pressure Ratio is Increased in Severe Diabetic Neurpathy and Can Predict Foot Ulceration," Diabetes Care, vol. 25, No. 6, Jun. 2002, pp. 1066-1071.
Chen et al. "Development of a Thermal and Hyperspectrial Imaging System for Wound Characterization and Metabolic Correlation," John Hopkins Apl Technical Digest, vol. 26, No. 1, 2005, pp. 67-74.
Chien et al. "Selection and ordering of feature observations in a pattern recognition system." Info and Control 12, No. 5. 1968, pp. 394-414.
Dabiri et al. "Electronic Orthotics Shoe: Preventing Ulceration in Diabetic Patients," 30th Annual International IEEE EMBS Conference, Aug. 2008, pp. 771-774.
Engler. "Rock Health Presentation" of Aug. 24, 2012, 19 pages.
Engler. Declaration of Jeffrey M. Engler under 37 CFR § 1.56, Feb. 28, 2016, 2 pages.
Frykberg et al. Feasibility and Efficacy of a Smart Mat Technology to Predict Development of Diabetic Plantar Ulcers, Diabetes Care, vol. 40, Jul. 2017, pp. 973-980.
International Search Report and Written Opinion for International Application No. PCT/US2013/030997, dated Jul. 8, 2013, 13 pages.
International Search Report and Written Opinion for International Application No. PCT/US2016/060638 dated Mar. 2, 2017, 11 pages.
International Search Report and Written Opinion for International Application No. PCT/US2019/056325, dated Dec. 23, 2019.
Isaac et al. "Angiosomal Interpretation of Dermal Thermometry in Patients at High Risk for Diabetic Foot Ulcers." in 2018 Diabetic Limb Salvage Conference, 1 page.
Kaabouch et al. "Predicting neurpathic ulceration: analysis of static temperature distributions in thermal images," Journal of biomedical Optics, vol. 15, Sec. 6, 2010, pp. 061715-1-061715-6.
Lavery et al. Unilateral remote temperature monitoring to predict future ulceration for the diabetic foot in remission. BMJ Open Diabetes Research and Care, 7(1), 2019, 7 pages.
Liu et al., "Automatic detection of diabetic foot complications with infrared thermography by asymmetric analysis," Journal of Biomedical Optics, 20(2), 2015, 11 pages.
Liu et al. "Infrared Dermal Thermography on Diabetic Feet Soles to Predict Ulcerations: a Case Study," Proc. Of SPIE, vol. 8572, 2013, pp. 85720N-1-85720N-9.
Liu et al. "Statistical analysis of spectrial data: a methodology for designing an intelligent monitoring system for the diabetic foot," Predicting neuropathic ulceration: analysis of static temperature distributions in thermal images, Journal of Biomedical Opitcs, vol. 18(12), Dec. 2013, pp. 126004-1-126004-11.
Medgadget.com "TempTouch for Foot Ulcer Detection," Xilas, Inc., Apr. 19, 2005, 2 pages.
Morley et al. "In Shoe-Multisensory Data Acquisition System," IEEE Transactions on Biomedical Engineering, vol. 48, No. 7, Jul. 2001, pp. 815-820.
Notice of Opposition to a European Patent—European Patent No. 2833783B1, dated May 31, 2018, 8 pages.
Roback "An overview of temperature monitoring devices for early detection of diabetic foot disorders," Linkoping University Post Print, 2010, 18 pages.
Siren Care "Siren Care—Best Diabetic Socks Tracking Your Foot Health," http://siren.care/how-it-works, Jan. 6, 2017, 4 pages.
Supplementary European Search Report for Application No. EP 13772800, dated Jun. 26, 2015, 7 pages.
Supplementary European Search Report for European Patent Application No. 16863080, dated Apr. 30, 2019, 12 pages.
Van Netten et al. "Infrared Thermal Imaging for Automated Detection of Daibetic Foot Complications" Journal of Diabetes Sceince and Technology, vol. 7, Issue 5, Sep. 2013, pp. 1122-1129.
Bharara et al. "Coming events cast their shadows before: detecting inflammation in the acute diabetic foot and the foot in remission," Diabetes/Metabolism Research and Reviews, 2012, vol. 28, pp. 15-20.
Gatt, A., et al., "Establishing Differences in Thermographic Patterns between the Various Complications in Diabetic Foot Disease," Hindawi International Journal of Endocrinology, vol. 2018, Article ID 98208295, Mar. 12, 2018, 8 pages.
International Preliminary Report on Patentabilty for International Application No. PCT/US2019/056325 dated Dec. 23, 2019, 13 pages [3891-12502].
Supplementary European Search Report for Application No. PCT/US2019056325, No. 19874565.5, dated Jun. 9, 2022 (7 pages) [3891-12506].
Theuma, F., et al., The Use of Smartphone-attached Thermography Camera in Diagnosis of Acute Lower Limb Ischemia, Society for Vascular Surgery, Submitted Feb. 19, 2017; Accepted Feb. 23, 2017, 1 page.

* cited by examiner

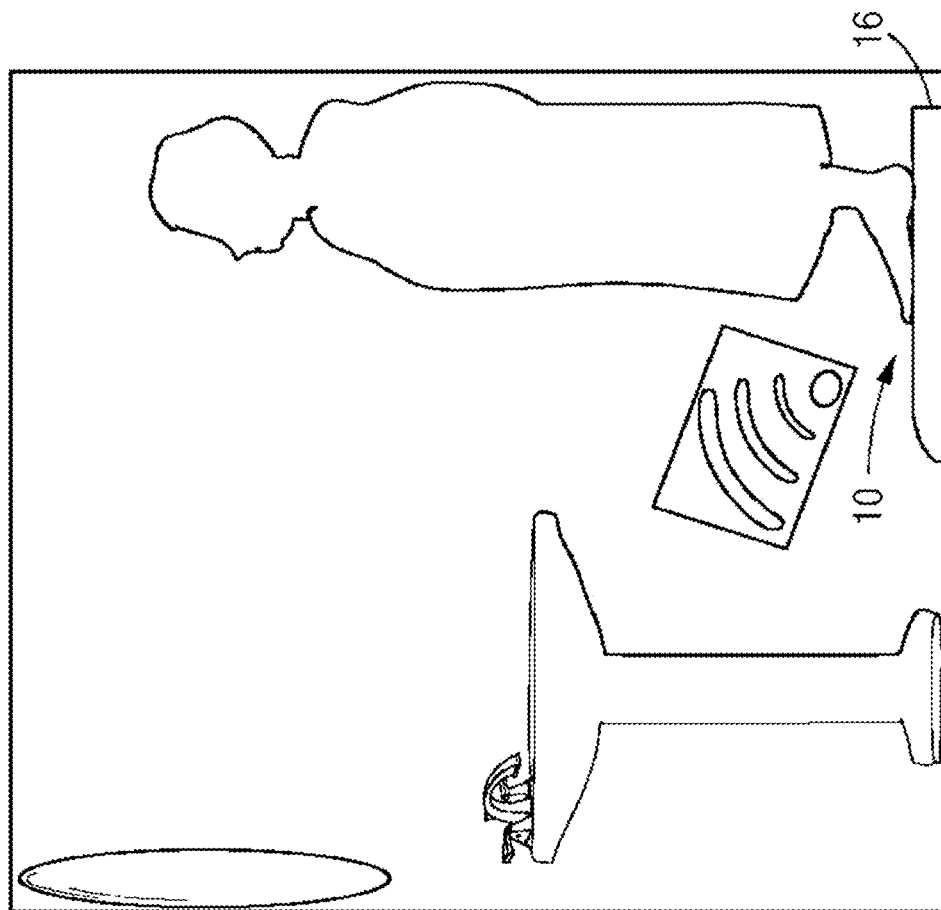
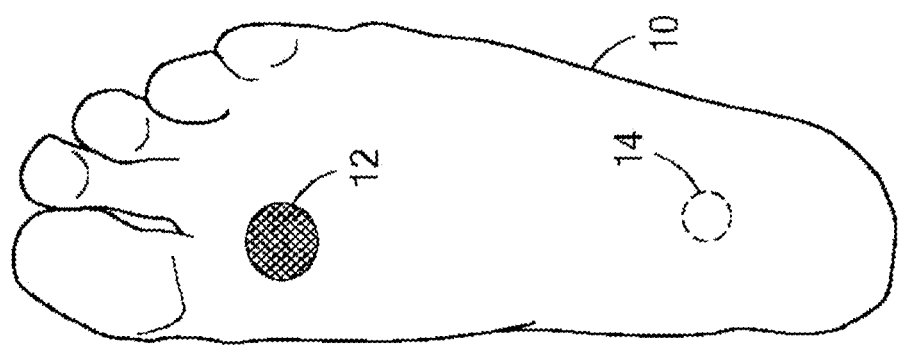
FIG. 2A
FIG. 1

IPSILATERAL ULCER AND PRE-ULCER DETECTION METHOD AND APPARATUS

PRIORITY

This patent application claims priority from provisional U.S. patent application No. 62/752,589, filed Oct. 30, 2018, entitled, "IPSILATERAL ULCER AND PRE-ULCER DETECTION METHOD AND APPARATUS," and naming David R. Linders and Brian Petersen as inventors, the disclosure of which is incorporated herein, in its entirety, by reference. This patent application also claims priority from provisional U.S. patent application No. 62/745,925, filed Oct. 15, 2018, entitled, "IPSILATERAL ULCER AND PRE-ULCER DETECTION METHOD AND APPARATUS," and naming David R. Linders and Brian Petersen as inventors, the disclosure of which is incorporated herein, other than "Commented" indicia at line 25 of page 22, in its entirety, by reference.

RELATED APPLICATIONS

This patent application is related to the following utility patent and its family members, the disclosure of which is incorporated herein, in its entirety, by reference:

U.S. Pat. No. 9,271,672, issued on Mar. 1, 2016, entitled, "METHOD AND APPARATUS FOR INDICATING EMERGENCE OF AN ULCER," and naming David Robert Linders, Jonathan David Bloom, Jeffrey Mark Engler, Brian Jude Petersen, Adam Geboff, and David Charles Kale, and as inventors.

FIELD OF THE INVENTION

Various embodiments of the invention generally relate to ulcers on living beings and, more particularly, various embodiments of the invention relate to systems for evaluating portions of living beings for ulcers.

BACKGROUND OF THE INVENTION

Open sores on an external surface of the body often form septic breeding grounds for infection, which can lead to serious health complications. For example, foot ulcers on a diabetic's foot can lead to gangrene, leg amputation, or, in extreme cases, death. The healthcare establishment therefore recommends monitoring a diabetic foot on a regular basis to avoid these and other dangerous consequences. Unfortunately, known techniques and systems for monitoring foot ulcers, among other types of ulcers, often are inconvenient to use, unreliable, or inaccurate, thus reducing compliance by the very patient populations that need it the most. It can be particularly difficult to use known techniques and systems to accurately monitor and locate ulcers and pre-ulcers on amputees and others with only one foot.

SUMMARY OF VARIOUS EMBODIMENTS

In accordance with one embodiment of the invention, a foot ulcer detection system has a body with a base having a top surface. The top surface of the base has a receiving region configured to receive the bottom of a single foot. Among other things, the base may be in the form of an open platform or a closed platform. The system also has a set of one or more temperature sensors in communication with the top surface of the receiving region of the platform. Specifically, the set of temperature sensors are spaced apart within the receiving region and configured to activate after receipt of a stimulus (e.g., receipt of a foot or a power signal energizing the sensors) applied to one or both the platform and the set of temperature sensors. The set of temperature sensors are configured to communicate with the bottom of the foot in the receiving region to ascertain a current temperature at each of a set of different spaced apart locations of the bottom of the foot. Accordingly, the set of temperature sensors are configured to produce a set of temperature values and thus, each location has one associated temperature value.

The system also has a comparator operatively coupled with the set of temperature sensors. The comparator is configured to determine a distribution of temperature values using the set of temperature values. The distribution has an interpercentile range between or including the zero percentile and the one hundred percentile of the set of temperature values (i.e., some or all of those temperature values, or one or more other temperature values within some range between the endpoints of the set of temperature values—those temperature values in the interpercentile may include number(s) not in the set of temperature values). The comparator further is configured to compare the interpercentile range to a threshold value. The system further has an output, operatively coupled with the comparator, that is configured to produce ulcer information relating to the emergence of an ulcer or pre-ulcer when the interpercentile range equals or exceeds the threshold value.

The output may be coupled with the body, or may be remote from the body (e.g., at a remote site across a network). Ulcer information may include data requiring further processing to indicate the emergence of an ulcer or pre-ulcer, or it may have information ready to present to a user in an understandable format. In a corresponding manner, the output and comparator may be spaced from and remote from the body.

In some embodiments, the set of temperature values includes a maximum temperature value and a minimum temperature value. In that case, the interpercentile range has the minimum temperature value at the zero percentile and the maximum temperature value at the one hundredth percentile. The interpercentile range may be between the zero percentile and the one hundredth percentile, or between one or two other percentiles. For example, the interpercentile range size may have a lowest temperature value greater than the zero percentile or a highest temperature value less than the one hundredth percentile. Moreover, the interpercentile range may have less than all of the temperature values in the set of temperature values (e.g., where the endpoints of the interpercentile range are not the minimum or maximum temperature values in the set of temperature values, or where only one of the noted endpoints is a minimum or maximum temperature value in the set of temperature values).

The threshold may be between approximately 1 degree C. and approximately 4 degrees C. (e.g., between approximately 1.4 degrees C. and approximately 2.8 degrees C.). Those skilled in the art may set the different locations to meet the application. For example, the set of different locations may be between four and one hundred locations (e.g., 4-6 locations) that relate to corresponding locations on the bottom of the foot.

Additional comparisons may further optimize the ability of the system to detect ulcers and pre-ulcers. For example, the system also may have a second comparator operably coupled with the output. The second comparator is configured to determine a tendency statistic (i.e., one of mean, median, and mode) from the set of temperature values. In addition, the second comparator also may be configured to produce a given value as a function of the tendency statistic and ambient temperature, and then compare the given value to a second threshold value. In this example, the output is configured to produce the ulcer information also as a function of the comparison of the given value to the second threshold value. Among other things, the comparator may be configured to produce the given value by determining the difference between the tendency statistic and the ambient temperature. The comparator may also be configured to produce the given value by determining the difference between the tendency statistic and some range value.

The comparator also may be configured to compare two of the sets of the temperature values to produce a comparison value, and then determine the difference between at least the comparison value and a third threshold value. In this case, the output is configured to produce the ulcer information as a function of the difference between the comparison value and the third threshold value.

In accordance with another embodiment, a method of detecting emergence of a foot ulcer or a foot pre-ulcer, communicates the bottom of a single foot with a modality (e.g., a closed platform, open platform, or a thermal camera). The closed or open platform includes a body having a base with a top surface having a receiving region configured to receive the bottom of a single foot. The receiving region has a set of temperature sensors in communication with (e.g., thermal or visual communication) the top surface of the receiving region, and the set of temperature sensors are spaced apart within the receiving region.

In a manner similar to other embodiments, the method activates the temperature sensors of the closed or open platform, and ascertains a current temperature at each of a set of different locations of the bottom of the foot after the foot is positioned in the receiving region of the base and in contact with the top surface of the base. Accordingly, this act produces a set of temperature values with each location having one associated temperature value. The method then produces a distribution of temperature values using the set of temperature values. The distribution has an interpercentile range comprising at least two of the set of temperature values. Next, the method compares the interpercentile range of temperatures to a threshold value, and produces electronic output information having information relating to the emergence of an ulcer or pre-ulcer when the interpercentile range size equals or exceeds the threshold value.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 1 schematically shows a foot having a prominent foot ulcer and a pre-ulcer.

FIG. 2A schematically shows one use and form factor that may be implemented in accordance with illustrative embodiments of the invention.

DESCRIPTION OF ILLUSTRATIVE EMBODIMENTS

Figure 2B:
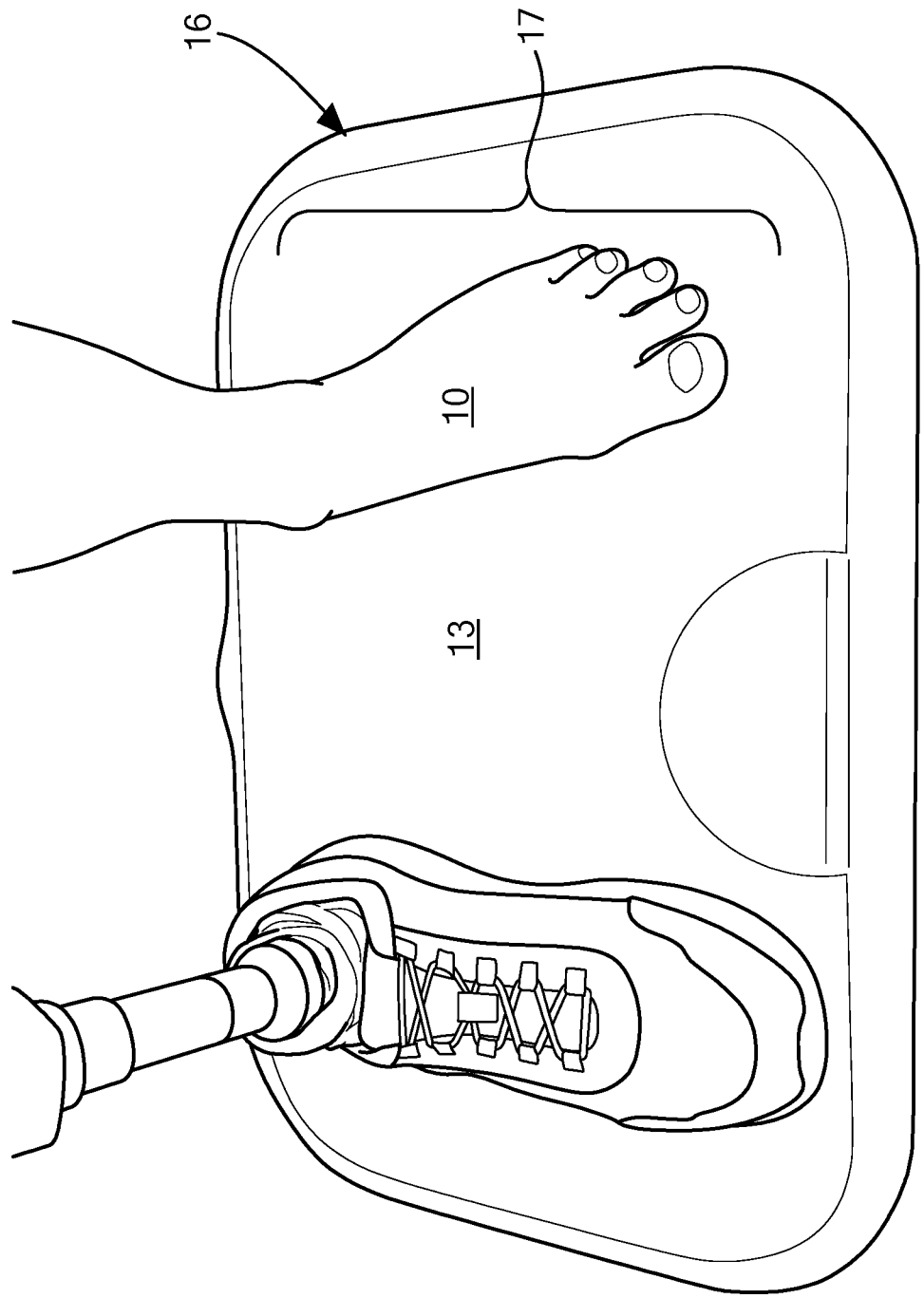
FIG. 2B schematically shows an open platform that may be configured in accordance with illustrative embodiments of the invention. This figure also shows use by an amputee with a single foot.

In illustrative embodiments, despite having less data than systems relying on two patient feet, a system effectively determines the existence of ulcers and pre-ulcers of patients with a single foot (e.g., amputees or patients with access to a single foot only, such as patients with a full foot and another partial foot). To that end, an ulcer detection system determines a interpercentile temperature range as a function of a distribution of temperature values across prescribed parts of a single foot, and then compares that range size to a threshold value. Next, the system produces output information indicating the emergence of an ulcer or pre-ulcer when the interpercentile temperature range size equals or exceeds the threshold value. Details of illustrative embodiments are discussed below.

As known by those in the art, routine foot temperature monitoring has been shown to be effective for identifying inflammation preceding foot ulcers or other inflammatory foot conditions. A traditional approach uses differences in temperatures between the right and left feet to characterize inflammation, and thus risk. Comparison of contralateral temperature differences is known as asymmetry analysis.

Some of the patients at elevated risk to develop inflammatory foot complications, however, have history of major lower extremity amputation, such as trans-femoral, trans-tibial, or ankle disarticulation. These patients thus suffer from a significant problem that the prior art cannot solve—they cannot rely on the traditional approaches for foot temperature monitoring to identify inflammation because they lack the required anatomy and only have one foot. Using specific platforms and/or techniques, illustrative embodiments aim to solve these problems by analyzing the temperatures of a single foot to determine various pathologies related to inflammation in the foot, such as diabetic foot ulcers, Charcot syndrome, claudication, and embolism.

Additionally, as discussed below, some patients may have only one foot available for foot temperature monitoring due to ongoing treatment of a wound to one foot or some other reason. As is well known by those skilled in the art, such treatment may require bandaging, casting, or use of a boot. These patients also are unable to rely on traditional approaches for foot temperature monitoring using prior art techniques known to the inventors.

Specifically, illustrative embodiments analyze a patient's foot to determine the risk of an ulcer emerging on its underside (i.e., on its sole). This permits patients, their healthcare providers, and/or their caregivers to intervene earlier, reducing the risk of more serious complications. To that end, a temperature detection modality (e.g., an open or closed platform) receives the patient's foot and generates temperature data that is processed to determine whether an ulcer or pre-ulcer will/has emerged, and/or the progression of a known ulcer or pre-ulcer. The modality may use any of a variety of different processes, discussed in detail below, such as comparing one or more portions of the foot, or an interpercentile range of temperatures, to some prescribed other value, such as the environmental/ambient temperature, a prescribed threshold, or the temperature of another portion of the foot.

Using that comparison, if the modality and/or its associated apparatus determines that the foot presents at least one of a number of prescribed patterns and/or meets certain thresholds/requirements, then various embodiments produce output information indicating whether an ulcer or pre-ulcer will/has emerged, and/or the progression of a known ulcer or pre-ulcer.

To analyze one foot, illustrative embodiments may use modalities and techniques similar to those discussed in U.S. Pat. No. 9,271,672. For example, FIG. 1 schematically shows a bottom view of a patient's foot 10 that, undesirably, has an ulcer 12 and a pre-ulcer 14 (described below and shown in phantom since pre-ulcers 14 do not break through the skin). As one would expect, an ulcer 12 on this part of the foot 10 typically is referred to as a "foot ulcer 12." Generally speaking, an ulcer is an open sore on a surface of the body generally caused by a breakdown in the skin or mucous membrane. Diabetics often develop foot ulcers 12 on the soles of their feet 10 as part of their disease. In this setting, foot ulcers 12 often begin as a localized inflammation that may progress to skin breakdown and infection.

It should be noted that discussion of diabetes and diabetics is but one example and used here simply for illustrative purposes only. Accordingly, various embodiments apply to other types of diseases (e.g., stroke, deconditioning, sepsis, friction, coma, etc.) and other types of ulcers—such embodiments may apply generally where there is a compression or friction on the living being's body over an extended period of time. For example, various embodiments also apply to ulcers formed on different parts of the body, such as on the back (e.g., bedsores), inside of prosthetic sockets, or on the buttocks (e.g., a patient in a wheelchair). Moreover, some embodiments apply to other types of living beings beyond human beings, such as other mammals (e.g., horses or dogs). Accordingly, discussion of diabetic human patients having foot ulcers 12 is for simplicity only and not intended to limit all embodiments of the invention.

Many prior art ulcer detection technologies known to the inventors suffered from one significant problem—patient compliance. If a diseased or susceptible patient does not regularly check his/her feet 10, then that person may not learn of an ulcer 12 or a pre-ulcer 14 until it has emerged through the skin and/or requires significant medical treatment. Accordingly, illustrative embodiments implement an ulcer monitoring system in any of a variety of forms—preferably in an easy to use form factor or modality that facilitates and encourages regular use. One such modality/form factor involves a platform having a base and receiving region for receiving the foot (both discussed in greater detail below).

FIGS. 2A and 2B schematically show one form factor, in which a patient/user steps on an open platform 16 that gathers data about that user's foot (or feet 10). As shown in FIG. 2A, the patient has only one natural foot with which to gather data for making an assessment. The other foot, in this embodiment, is a prosthetic. Other embodiments may operate without a prosthetic foot, or even with only a single foot that itself has amputations (e.g., a single foot with only three toes).

In this example, the open platform 16 is in the form of a base implemented as a floor mat placed in a location where he the patient regularly stands, such as in front of a bathroom sink, next to a bed, in front of a shower, on a footrest, or integrated into a mattress. As an open platform 16, the patient simply may step on the top sensing surface 13 of the platform 16 (e.g., using a prosthetic where the other foot would have been, or supported by some object) to initiate the process. Accordingly, this and other form factors often do not require that the patient affirmatively decide to interact with the platform 16. Instead, many expected form factors are configured to be used in areas where the patient frequently stands during the course of their day without a foot covering. Alternatively, the open platform 16 may be moved to directly contact the feet 10 of a patient that cannot stand. For example, if the patient is bedridden, then the platform 16 may be brought into contact with the patient's feet 10 while in bed. In this example, the patient's foot may be placed into a receiving region of the platform 16 to begin foot analysis.

A bathroom mat or rug are but two of a wide variety of different potential form factors. Others may include a platform 16 resembling a scale, a stand, a footrest, a console, a tile built into the floor, or a more portable mechanism that receives at least one of the feet 10. The implementation shown in FIGS. 2A and 2B has a top surface area that is larger than the surface area of the foot 10 of the patient. In preferred embodiments, the receiving region is large enough to receive the foot 10. This enables a caregiver to obtain a complete view of the patient's entire sole, providing a more complete view of the foot 10.

The open platform 16 of various embodiments also has some indicia or display 18 on its top surface 13 that can have any of a number of functions. For example, the indicia/display 18 can turn a different color or sound an alarm after the readings are complete, show the progression of the process, or display results of the process. Of course, the indicia or display 18 can be at any location other than on the top surface 13 of the open platform 16, such as on the side, or a separate component that communicates with the open platform 16. In fact, in addition to, or instead of, using visual or audible indicia, the platform 16 may have other types of indicia, such as tactile indicia/feedback, our thermal indicia.

Rather than using an open platform 16, alternative embodiments may be implemented as a closed platform 16, such as a shoe, shoe insert, insole, slipper or sock that can be regularly worn by a patient, or worn on an as-needed basis. For example, the insole of the patient's shoe or boot may have the functionality for detecting the emergence of a pre-ulcer 14 or ulcer 12, and/or monitoring a pre-ulcer 14 or ulcer 12. Positioning the foot appropriately in such a platform to the receiving region thus should be easier since the closed platform 16 may include features that guide the foot to the appropriate location (e.g., the natural outside of the platform 16, specialized extra elements, or other apparatus).

To monitor the health of the patient's foot (discussed in greater detail below), the platform 16 of FIGS. 2A and 2B gathers temperature data about a plurality of different locations on the sole of the foot 10. This temperature data provides the core information ultimately used to determine the health of the foot 10. FIG. 3 schematically shows an exploded view of the open platform 16 configured and arranged in accordance with one embodiment of the invention. Of course, this embodiment is but one of a number of potential implementation and, like other features, is discussed by example only.

Figure 3A:
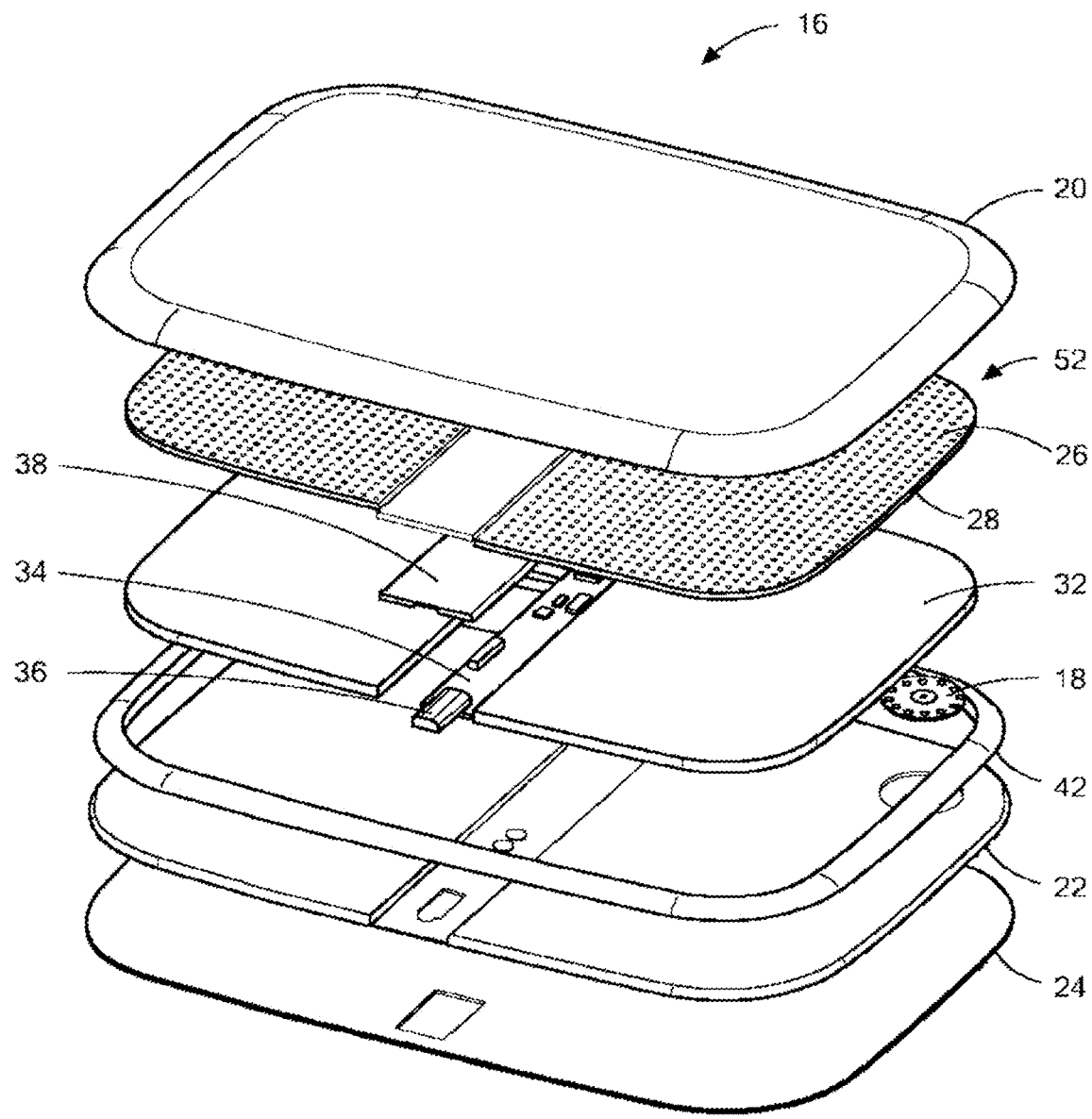
FIG. 3A schematically shows an exploded view of one type of open platform that may be configured in accordance with illustrative embodiments of the invention.

As shown, the platform 16 is formed as a stack of functional layers sandwiched between a cover 20 and a rigid base 22. For safety purposes, the base 22 preferably has rubberized or has other non-skid features on its bottom side. FIG. 3A shows one embodiment of this non-skid feature as a non-skid base 24. The platform 16 preferably has relatively thin profile to avoid tripping the patient and making it easy to use.

To measure foot temperature, the platform 16 has a receiving region 17 on the top platform surface for receiving the foot 10. This receiving region 17 is specially configured to communicate with the underside of the foot1 10. In this embodiment, the receiving region 17 has an array, matrix, or other prescribed arrangement of temperature sensors 26 fixed in place directly underneath the cover 20. More specifically, the temperature sensors 26 are positioned on a relatively large printed circuit board 28. The sensors 26 preferably are laid out in a two-dimensional array/matrix of stationary contact sensors on the printed circuit board 28. In some embodiments, the pitch or distance between the preferably may be relatively small, thus permitting more temperature sensors 26 on the array. Among other things, the temperature sensors 26 may include temperature sensitive resistors (e.g., printed or discrete components mounted onto the circuit board 28), graphene temperature sensors, thermocouples, fiberoptic temperature sensors, or a thermochromic film. Accordingly, when used with temperature sensors 26 that require direct contact, illustrative embodiments form the cover 20 with a thin material having a relatively high thermal conductivity. The platform 16 also may use temperature sensors 26 that can still detect temperature through a patient's socks.

Other embodiments may use noncontact temperature sensors 26, such as infrared detectors. Indeed, in that case, the cover 20 may have openings to provide a line of sight from the sensors 26 to the sole of the foot 10. Accordingly, discussion of contact sensors is by example only and not intended to limit various embodiments. As discussed in greater detail below and noted above, regardless of their specific type, the plurality of sensors 26 generate a plurality of corresponding temperature data values for a plurality of portions/spots on the patient's foot 10 to monitor the health of the foot 10.

Some embodiments, however, may have a smaller number of temperature sensors 26 that are spaced apart (e.g., the distance between the sensors 26 is many times the largest dimension of the sensors 26 themselves, such as ten times or more). For example, as discussed below, some embodiments of the receiving region 17 may have as few as four or six sensors 26 spaced apart at prescribed portions of the platform (e.g., see FIG. 9, discussed below). Use of fewer temperature sensors 26 may be assisted by indicia or other means for directing a patient on the appropriate location for their foot to contact the top surface 13 of the cover 20—to align the foot with the appropriate sensors 26. Illustrative embodiments with a larger array of temperature sensors 26, however, may not require such assistance. Instead, such latter embodiments may determine the orientation and location of specific sensors to determine the desired smaller number of temperature values required (see below processes for further information on this process).

Some embodiments thus also may use pressure sensors for various functions, such as to determine the orientation of the feet 10 and/or to automatically begin the measurement process. Among other things, the pressure sensors may include piezoelectric, resistive, capacitive, or fiber-optic pressure sensors. This layer of the platform 16 also may have additional sensor modalities beyond temperature sensors 26 and pressure sensors, such as positioning sensors, GPS sensors, accelerometers, gyroscopes, and others known by those skilled in the art.

Accordingly, illustrative embodiments for performing thermal analysis of a foot may obtain temperature input from a variety of sensor types, including thermal cameras, open platforms with contact or non-contact temperature sensors, socks, shoes, insoles, bandages, wraps, individual point temperature measurements by hand. Temperature sensors may include infrared photodiodes, phototransistors, resistive temperature detectors, thermistors, thermocouples, fiberoptic, thermochromic sensors. Those skilled in the art should understand that these temperature sensing modalities and sensor types are examples of options available for use, and that some or all of the analysis methods described below are not dependent on the sensor modality employed in the system.

Figure 3B:
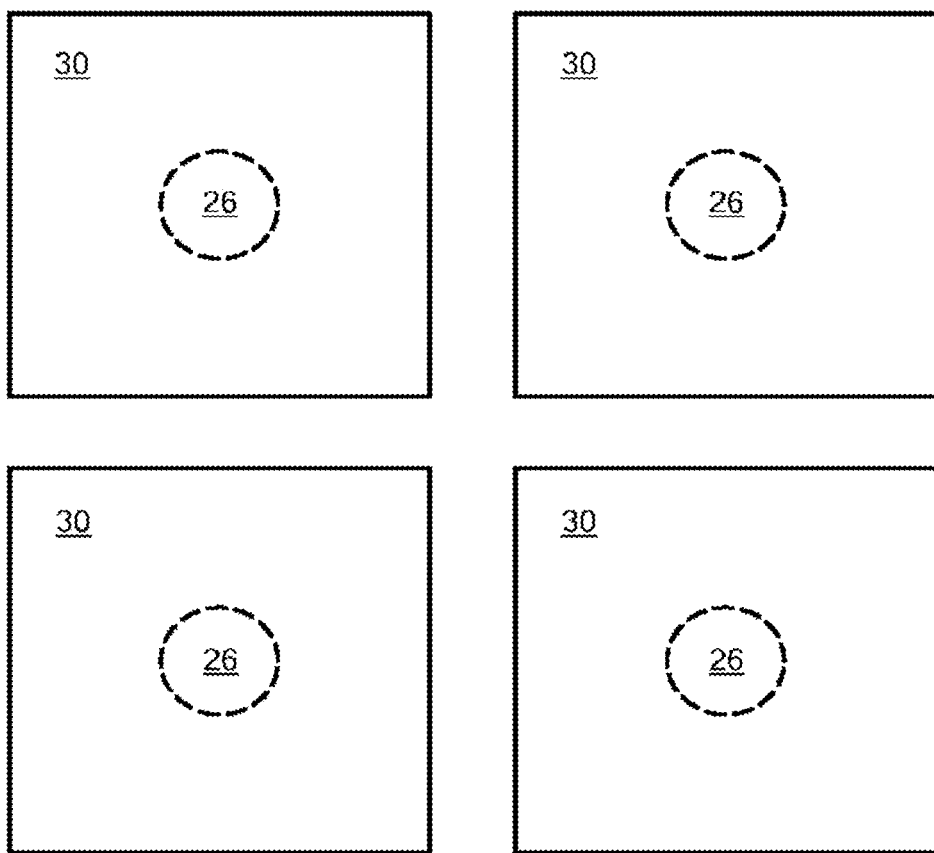
FIG. 3B schematically shows a close-up view of the platform with details of the pads and temperature sensors in the foot receiving region.

To reduce the time required to sense the temperature at specific points, illustrative embodiments position an array of heat conducting pads 30 over the array of temperature sensors 26. To illustrate this, FIG. 3B schematically shows a small portion of the array of temperature sensors 26 showing four temperature sensors 26 and their pads 30. The temperature sensors 26 are drawn in phantom because they preferably are covered by the pads 30. Some embodiments do not cover the sensors 26, however, and simply thermally connect the sensors 26 with the pads 26.

Accordingly, each temperature sensor 26 in this embodiment has an associated heat conducting pad 30 that channels heat from one two-dimensional portion of the foot 10 (considered a two dimensional area although the foot may have some depth dimensionality) directly to its exposed surface 13. The array of conducting pads 30 preferably takes up the substantial majority of the total surface area of the printed circuit board 28. The distance between the pads 30 thermally isolates them from one another, thus eliminating thermal short-circuits.

For example, each pad 30 may have a square shape with each side having a length of between about 0.1 and 1.0 inches. In the larger sensor arrays, the pitch between pads 30 thus is less than that amount. Accordingly, as a further detailed example, some embodiments may space the temperature sensors 26 about 0.4 inches apart with 0.25 inch (per side) square pads 30 oriented so that each sensor 26 is at the center of the square pads 30. This leaves an open region (i.e., a pitch) of about 0.15 inches between the square pads 30. Among other things, the pads 30 may be formed from a film of thermally conductive metal, such as a copper. Some embodiments that use fewer sensors 26, such as those that use six sensors to align with prescribed portions of the foot (e.g., see FIG. 9, discussed below), may space the pads farther apart to gather data about one specific sector/portion of the foot 10.

As suggested above, some embodiments do not use an array of temperature sensors 26. Instead, such embodiments may use a single temperature sensor 26 that can obtain a temperature reading of most or all of the sole. For example, a single sheet of a heat reactive material, such as a thermochromic film (noted above), or similar apparatus should suffice. As known by those in the art, a thermochromic film, based on liquid crystal technology, has internal liquid crystals that reorient to produce an apparent change in color in response to a temperature change, typically above the ambient temperature. Alternatively, one or more individual temperature sensors 26, such as thermocouples or temperature sensor resistors, may be movable to take repeated temperature readings across the bottom of the foot 10. Other embodiments may have a plurality of temperature sensors 26 that provide enough data to form a thermogram. In a manner to the thermochromic film example, specific locations of interest may be used to perform various comparisons and analyses. A thermal camera also may be integrated into one of the noted modalities, used in conjunction with another of those modalities (e.g., an open or closed platform in that case may not use temperature sensors 26 in that case), or used with the relevant system components in place of one of the noted modalities.

In various other embodiments, the base 22 of the platform/modality may include other similar structure that supports various other components, such as, in some cases, temperature sensors 26. For example, a closed platform 16 implemented as a shoe, the base 22 may include the insole.

To operate efficiently, the open platform 16 should be configured so that its top surface 13 contacts substantially the entire sole of the patient's foot 10. To that end, the platform 16 has a flexible and movable layer of foam 32 or other material that at least generally conforms to the user's foot 10. For example, this layer should conform to the arch of the foot 10. Of course, the sensors 26, printed circuit board 28, and cover 20 also may be similarly flexible and yet robust to conform to the foot 10 in a corresponding manner. Accordingly, the printed circuit board 28 preferably is formed largely from a flexible material that supports the circuit. For example, the printed circuit board 28 may be formed primarily from a flex circuit that supports the temperature sensors 26, or it may be formed from strips of material that individually flex when receiving feet. Alternative embodiments may not have such flexibility (e.g., formed from conventional printed circuit board material, such as FR-4) and thus, produce less effective data.

The rigid base 22 positioned between the foam 32 and the non-skid base 24 provides rigidity to the overall base structure. In addition, the rigid base 22 is contoured to receive a motherboard 34, a battery pack 36, a circuit housing 38, and additional circuit components that provide further functionality. For example, the motherboard 34 may contain integrated circuits and microprocessors that control the functionality of the platform 16.

In addition, the motherboard 34 also may have a user interface/indicia display 18 as discussed above, and a communication interface to connect to a larger network 44, such as the Internet. The communication interface may connect wirelessly or through a wired connection with the larger network 44, implementing any of a variety of different data communication protocols, such as Ethernet. Alternatively, the communication interface 40 can communicate through an embedded Bluetooth or other short range wireless radio that communicates with a cellular telephone network 44 (e.g., a 3G or 4G network).

The platform 16 also may have edging 42 and other surface features that improve its aesthetic appearance and feel to the patient. The layers may be secured together using one or more of an adhesive, snaps, nuts, bolts, or other fastening devices. The platform 16 may also be tapered at its edges to prevent the platform 16 from being a tripping hazard to the user.

Figure 4:
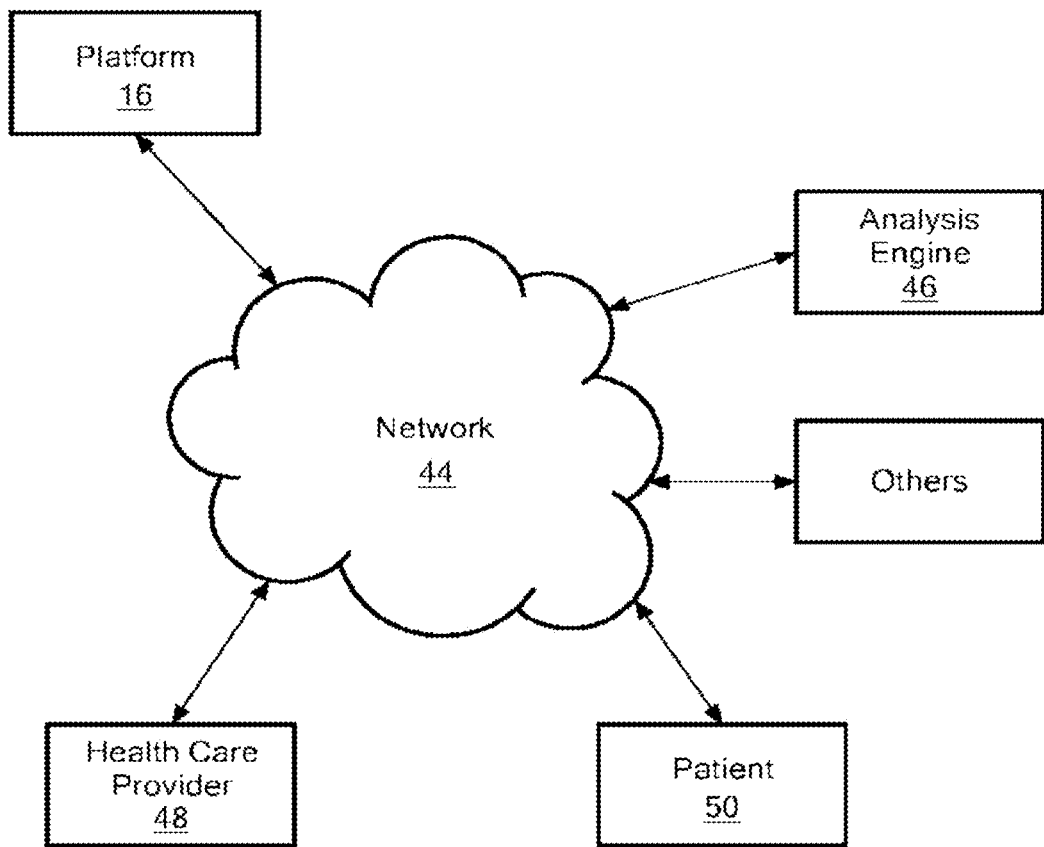
FIG. 4 schematically shows a network implementing illustrative embodiments of the invention.

Although they gather temperature and other data about the patient's foot, illustrative embodiments may locate additional logic for monitoring foot health at another location. For example, such additional logic may be on a remote computing device. To that and other ends, FIG. 4 schematically shows one way in which the platform 16 can communicate with a larger data network 44 in accordance with various embodiments the invention. As shown, the platform 16 may connect with the Internet through a local router, through its local area network, or directly without an intervening device. This larger data network 44 (e.g., the Internet) can include any of a number of different endpoints that also are interconnected. For example, the platform 16 may communicate with an analysis engine 46 that analyzes the thermal data from the platform 16 and determines the health of the patient's foot 10. The platform 16 also may communicate directly with a healthcare provider 48, such as a doctor, nurse, relative, and/or organization charged with managing the patient's care. In fact, the platform 16 also can communicate with the patient, such as through text message, telephone call, e-mail communication, or other modalities as the system permits.

Figure 5:
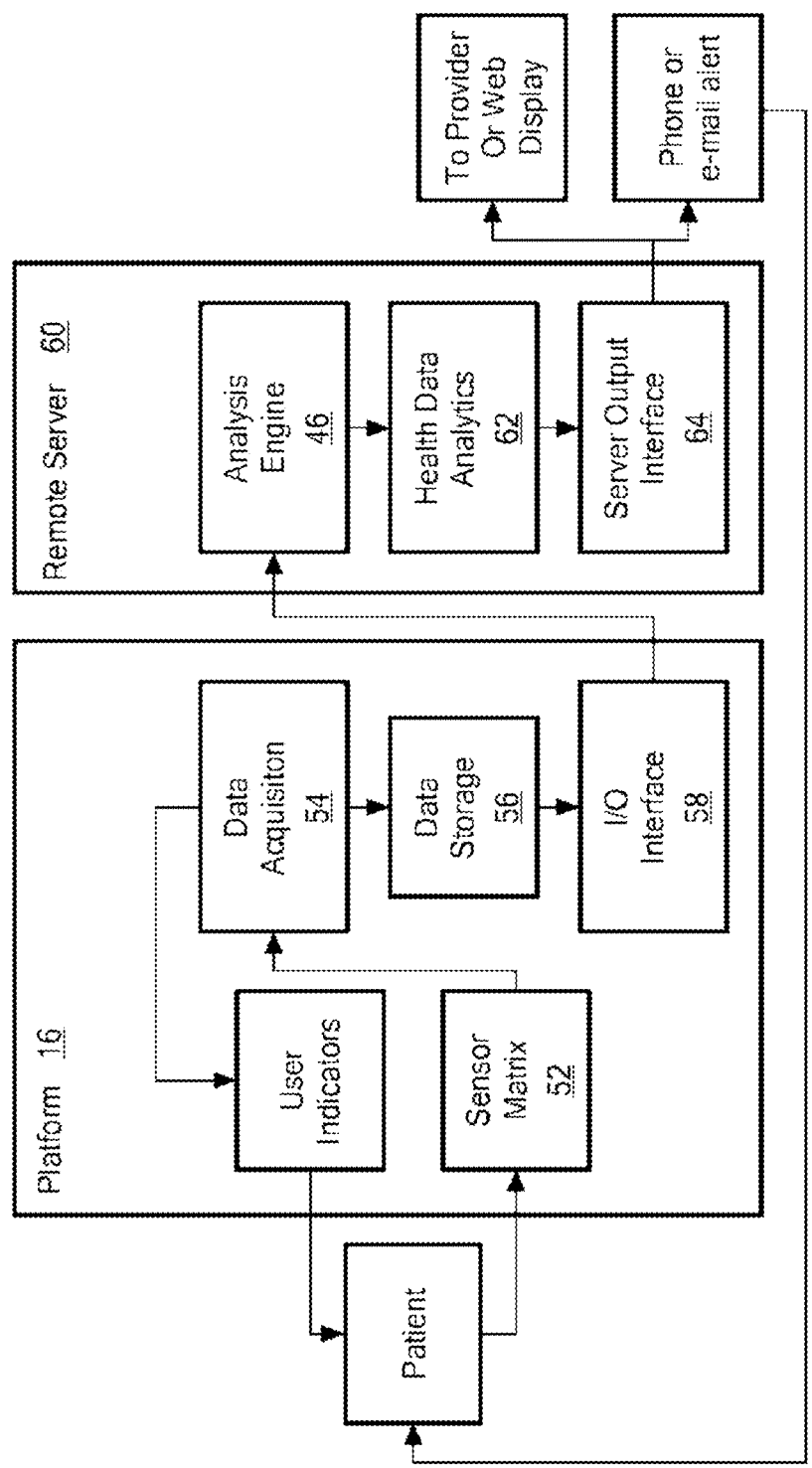
FIG. 5 schematically shows an overview of various components of illustrative embodiments of the invention.

FIG. 5 schematically shows a block diagram of a foot monitoring system, showing the platform 16 and the network 44 with its interconnected components in more detail. As shown, the patient communicates with the platform 16 by standing on or being received in some manner by the receiving region 17 having the sensors 26, which is represented in this figure as a "sensor matrix 52" (although other embodiments of the sensors 26 are not arranged as a matrix). A data acquisition block 54, implemented by, for example, the motherboard 34 and circuitry shown in FIG. 3, controls acquisition of the temperature and other data for storage in a data storage device 56. Among other things, the data storage device 56 can be a volatile or nonvolatile storage medium, such as a hard drive, high-speed random-access-memory ("RAM"), or solid-state memory. The input/output interface port 58, also controlled by the motherboard 34 and other electronics on the platform 16, selectively transmits or forwards the acquired data from the storage device to the analysis engine 46 on a remote computing device, such as a server 60. The data acquisition block 54 also may control the user indicators/displays 18, which provide feedback to the user through the above mentioned indicia (e.g., audible, visual, or tactile).

The analysis engine 46, on the remote server 60, analyzes the data received from the platform 16 in conjunction with a health data analytics module 62. A server output interface 64 forwards the processed output information/data from the analysis engine 46 and health data analytics module 62 toward others across the network 44, such as to a provider, a web display, or to the user via a phone, e-mail alert, text alert, or other similar way.

This output message may have the output information in its relatively raw form for further processing. Alternatively, this output message may have the output information formatted in a high-level manner for easy review by automated logic or a person viewing the data. Among other things, the output message may indicate the actual emergence of an ulcer 12 or a pre-ulcer 14, the risk of the emergence of an ulcer 12 or a pre-ulcer 14, or simply that the foot 10 is healthy and has no risks of ulcer 12 or pre-ulcer 14. In addition, this output message also may have information that helps an end-user or healthcare provider 48 monitor an ulcer 12 or pre-ulcer 14.

Using a distributed processing arrangement like that shown in FIG. 5 has a number of benefits. Among other things, it permits the platform 16 to have relatively simple and inexpensive components that are unobtrusive to the patient. Moreover, this permits a "software-as-a-service" business model ("SAAS model"), which, among other things, permits more flexibility in the functionality, typically easier patient monitoring, and more rapid functional updates. In addition, the SAAS model facilitates accumulation of patient data to improve analytic capability.

Some embodiments may distribute and physically position the functional components in a different manner. For example, the platform 16 may have the analysis engine 46 on its local motherboard 34. In fact, some embodiments provide the functionality entirely on the platform 16 and/or within other components in the local vicinity of the platform 16. For example, all of those functional elements (e.g., the analysis engine 46 and other functional elements) may be within the housing formed by the cover 20 and the rigid base 22. Accordingly, discussion of a distributed platform 16 is but one of a number of embodiments that can be adapted for a specific application or use.

Figure 6:
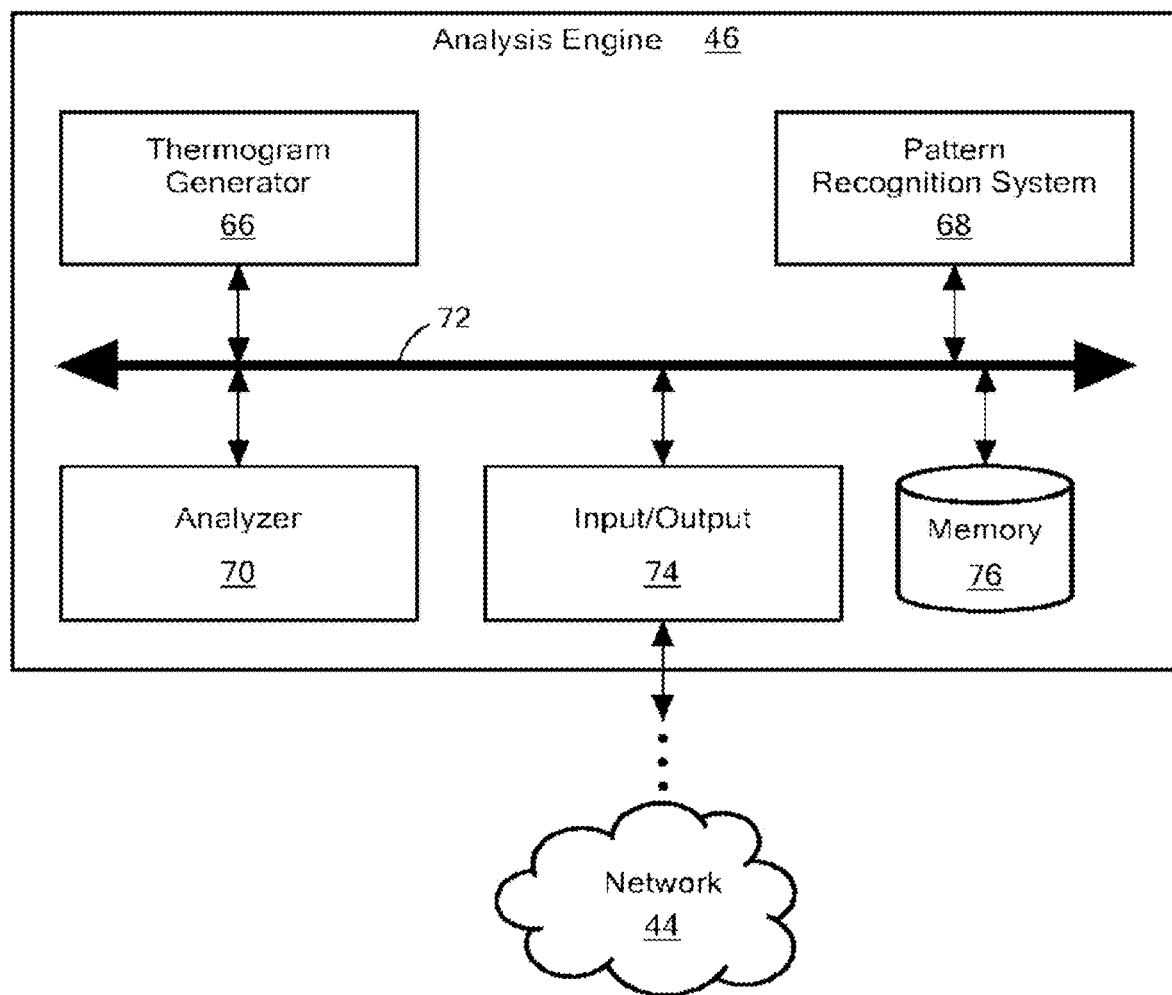
FIG. 6 schematically shows details of a data processing module in accordance with illustrative embodiments of the invention.

Those skilled in the art can perform the functions of the analysis engine 46 using any of a number of different hardware, software, firmware, or other non-known technologies. FIG. 6 shows several functional blocks that, with other functional blocks, may be configured to perform the functions of the analysis engine 46. This figure simply shows the blocks and is illustrative of one way of implementing various embodiments.

Among other things, the analysis engine 46 of FIG. 6 may have a thermogram generator 66 configured to form a thermogram of the patient's foot 10 or feet 10 (if a thermogram is to be used in the analysis) based on a plurality of temperature readings from the bottom of the foot 10, and a pattern recognition system 68 configured to determine whether the thermogram presents any of a number of different prescribed patterns. Pattern data and other information may be stored in a local memory 76. As discussed below, if the thermogram and/or the plurality of temperature readings presents any of these prescribed patterns, then the foot 10 may be unhealthy in some manner (e.g., having a pre-ulcer 14 or an ulcer 12).

The analysis engine 46 also has an analyzer 70 configured to produce the above noted output information, which indicates any of a number of different conditions of the foot 10. For example, the output information may indicate the risk that an ulcer 12 will emerge, the emergence of a pre-ulcer 14 (i.e., the first indication of a pre-ulcer 14), the progression of a known ulcer 12, or the emergence of a new ulcer 12 (i.e., the first indication of any given ulcer 12 to the patient and associated support). Communicating through some interconnect mechanism, such as a bus 72 or network connection, these modules cooperate to determine the status of the foot 10, which may be transmitted or forwarded through an input/output port 74 that communicates with the prior noted parties across the larger data network 44.

Indeed, it should be noted that FIGS. 5 and 6 only schematically show each of the noted components and a single embodiment. Those skilled in the art should understand that each of these components can be implemented in a variety of conventional manners, such as by using hardware, software, or a combination of hardware and software, across one or more other functional components. For example, the analyzer 70 may be implemented using a plurality of microprocessors executing firmware. As another example, the analyzer 70 may be implemented using one or more application specific integrated circuits (i.e., "ASICs") and related software, or a combination of ASICs, discrete electronic components (e.g., transistors), and microprocessors. Accordingly, the representation of the analyzer 70 and other components in a single box of FIG. 5 is for simplicity purposes only. In fact, in some embodiments, the analyzer 70 of FIG. 5 is distributed across a plurality of different machines—not necessarily within the same housing or chassis.

Illustrative embodiments use one or combinations of various methods/processes/techniques, along with prescribed physical modalities, to assess and make determinations about foot health using a single foot only. Specifically, illustrative embodiments may use one or combinations of one or more methods/techniques to make ipsilateral temperature comparisons. To make those assessments and determinations, illustrative embodiments use a comparator 80, such as that shown in FIG. 7. As previously noted, the comparator 80 can be used as part of the system of FIG. 5 (e.g., part of the analysis engine 46 or other component of the analysis engine 46), as a separate component local to or remote from the platform 16, or as an adjunct with the system of FIG. 5.

Figure 7:
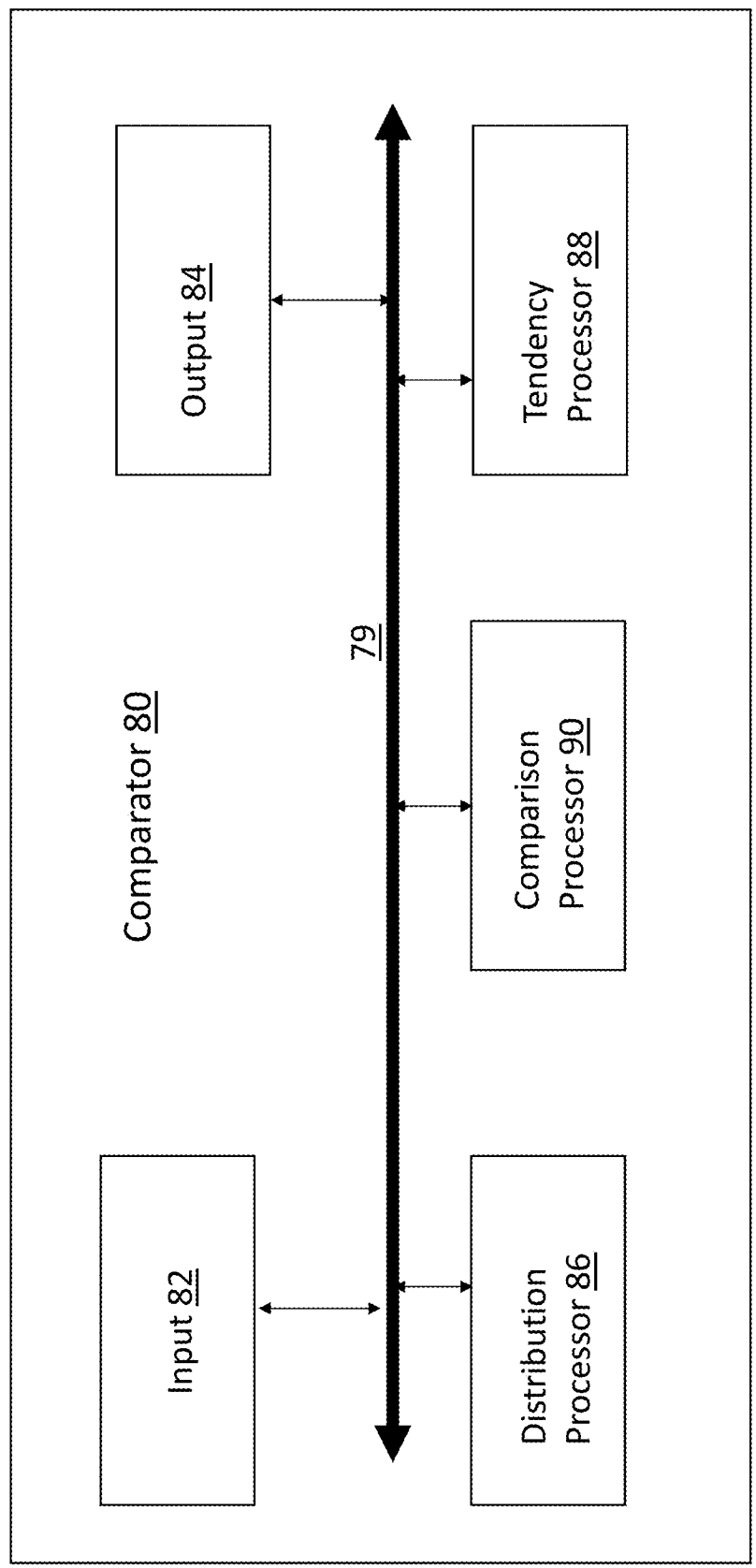
FIG. 7 schematically shows a comparator configured in accordance with illustrative embodiments of the invention.

Each of these components is operatively connected by any conventional interconnect mechanism. FIG. 7 simply shows a bus 79 communicating each the components. Those skilled in the art should understand that this generalized representation can be modified to include other conventional direct or indirect connections. Accordingly, discussion of a bus is not intended to limit various embodiments.

As with other systems discussed above, it should be noted that FIG. 7 only schematically shows each of these components. Accordingly, in a similar manner, those skilled in the art should understand that each of these components can be implemented in a variety of conventional manners, such as by using hardware, software, or a combination of hardware and software, across one or more other functional components. For example, a distribution processor 86 may be implemented using a plurality of microprocessors executing firmware. As another example, the distribution processor 86 may be implemented using one or more application specific integrated circuits (i.e., "ASICs") and related software, or a combination of ASICs, discrete electronic components (e.g., transistors), and microprocessors. Accordingly, the representation of the distribution processor 86 and other components in a single box of FIG. 7 is for simplicity purposes only. In fact, in some embodiments, the distribution processor 86 is distributed across a plurality of different machines—not necessarily within the same housing or chassis.

It should be reiterated that the representation of FIG. 7 is a simplified representation of an actual comparator. Those skilled in the art should understand that such a device may have many other physical and functional components, such as central processing units, other data processing modules, and short-term memory. Accordingly, this discussion is in no way intended to suggest that FIG. 7 represents all of the elements of a comparator.

As with many devices, the comparator 80 has an input 82 for receiving data and an output 84 for processing and/or forwarding processed data. The output 84 and other components may be part of the same physical device (e.g., coupled with the platform 16 or base 22), or separate (e.g., components across the Internet or other network). The output data may have additional functionality to, either alone or with other components, produce ulcer information relating to the emergence of an ulcer or pre-ulcer. The comparator 80 also has a distribution processor 86 configured to determine the distribution of temperature values produced by the temperature sensors 26, and a tendency processor 88 to determine tendency data from the temperature values (e.g., the mean, median, and/or mode).

The comparator 80 also has a comparison processor 90 configured to compare various values. Among other things, the comparison processor 90 may effectively form one or more comparison processors 90 to compare various items, such as an interpercentile range to a threshold value, or to compare a tendency statistic to another threshold value. Indeed the comparison processor 90 may have the functionality to make other comparisons. Accordingly, as noted above, representation of the comparison processor 90 as a single box in the figure is merely schematic and not intended to imply a single comparison processor 90 with a single function.

As noted above, in illustrative embodiments, the system determines an interpercentile range of temperatures at prescribed portions of the single foot using a temperature distribution, and compares the that range with a prescribed threshold value. If size of the range is equal to or exceeds the threshold value, then the system may indicate that the single foot may require further assistance due to a potential ulcer or pre-ulcer. In fact, the results in some embodiments may also indicate a potentially ischemic condition with the single foot.

More specifically, as known by those in the art, a temperature distribution in this context includes a statistical function that describes the possible temperatures values and likelihoods of those values sampled on the foot. Instead or in addition, the temperature distribution also may comprise a finite set of specific temperature values, including a set having the measured temperature values only, or a set having the measured temperature values and other temperature values derived from the measured temperature values. Some of the data in the distribution may be calculated and/or some of the data in the distribution may be actual (e.g., actual temperature detected by a temperature sensor 26).

The data in a temperature distribution is considered to form a plurality of percentiles. For example, if the distribution has 100 different temperature values, each temperature value would by definition be in a different percentile—from the zero percentile to the one hundredth percentile (in this case, each would be a whole number percentile). Illustrative embodiments take advantage of a range of these percentiles, known as the "interpercentile range" (discussed above and below) to determine foot health. In particular, the interpercentile range is the difference of temperature values at two different percentiles in the dynamic range. For example, to calculate the interpercentile range, some embodiments may determine the difference between the end-point percentiles (e.g., the zero percentile and the one hundred percentile values), while others may determine the difference between temperature values (either estimated/interpolated/calculated or actual) between other percentiles. Still other embodiments may use temperature values at one of the end-point percentiles and some other non-end-point percentile (e.g., between the zero percentile and the ninetieth percentile). Those skilled in the art can select the appropriate interpercentile range.

Figure 8:
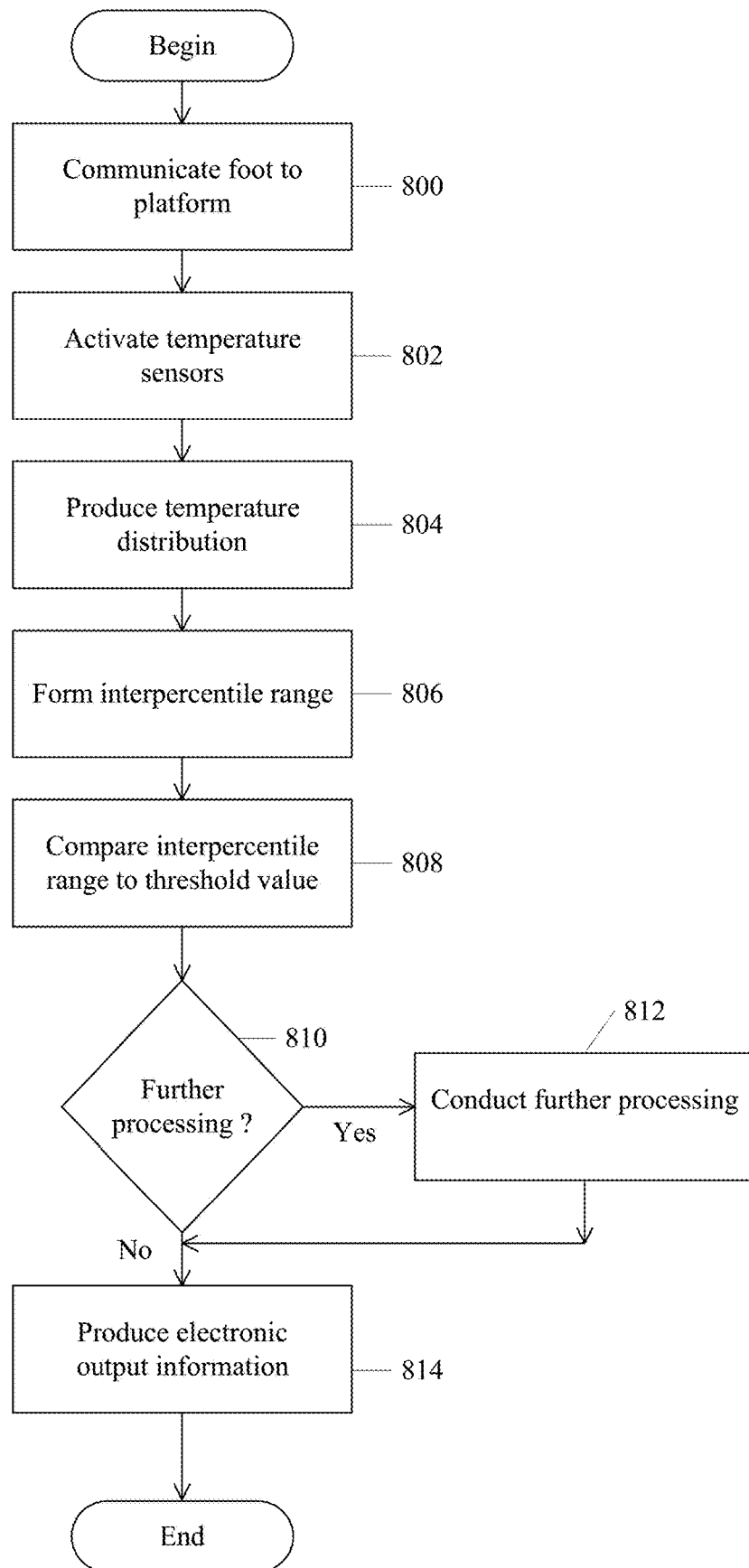
FIG. 8 shows a process of identifying potential ulcers and pre-ulcers for a single foot only in accordance with illustrative embodiments of the invention.

To those ends, FIG. 8 shows a process of identifying potential ulcers and pre-ulcers for a single foot only in accordance with illustrative embodiments of the invention.

It should be noted that this process (and others discussed below) is substantially simplified from a longer process that normally would be used to identify potential ulcers and pre-ulcers. Accordingly, the process can have other steps that those skilled in the art likely would use. In addition, some of the steps may be performed in a different order than that shown, or at the same time. Those skilled in the art therefore can modify the process as appropriate.

The process of FIG. 8 begins at step 800, in which the foot communicates with the receiving region 17 of the platform 16. To that end, if using the modality shown in FIGS. 2A and 2B, the patient may step onto the top surface 13 of the open platform 16. In illustrative embodiments that have fewer but spaced apart temperature sensors 26, the single, natural foot 10 of the patient preferably stands on the receiving region 17 of the platform 16, such as the portion having the spaced apart temperature sensors 26. In closed platform embodiments, the patient may insert their foot into a shoe, sock or similar device and contact the foot receiving region 17 in that modality. The temperature sensors 26 may directly or indirectly conductively contact the foot, or may contact the foot in other ways, such as using optics to take non-contact temperature measurements at the specific foot locations. The top surface 13 may be considered to act at least in part as the input 82 to the comparator 80 of FIG. 7.

Figure 9:
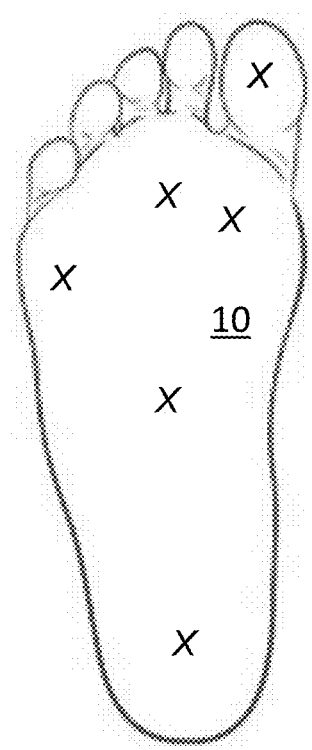
FIG. 9 schematically shows the bottom of a single foot and regions of that foot to receive temperature information in accordance with illustrative embodiments of the invention.

FIG. 9 schematically shows the general positions of the temperature sensors 26 relative to the bottom of the foot, when the foot 10 is properly positioned in the receiving region 17, in illustrative embodiments of the invention. Indeed, some embodiments may have six sensors 26, while others may have more or fewer (e.g., four sensors, six sensors, one hundred sensors, or a range between two of those numbers). The sensor locations in this figure are shown generically with an "X."

Returning to FIG. 8, the process continues to step 802, which activates the temperature sensors 26. Among other ways, the temperature sensors 26 may be activated manually, automatically, or virtually before, during, or after the patient communicates their foot to the platform 16. For example, power may be applied to the temperature sensors 26 by manually selecting or switching a power switch to an on position, virtually switching on the power via a software application, or automatically by logic or contact sensor (not shown) on the platform 16 sensing the foot 10 in the receiving region 17.

Next, the distribution processor 86 produces a distribution of the temperatures detected by the temperature sensors 26 (804) and, using that distribution, forms the interpercentile range (step 806). To that end, the distribution processor 86 may determine the percentiles of the data from the temperature distribution, and then determine which two percentiles to use to form the interpercentile range. That may be a simple process of simply taking the difference between the maximum and minimum temperature values (i.e., the end-points of the temperature range). Other embodiments, however, may be configured, either manually or automatically (e.g., using a database), to select some other percentile within the temperature range. For example, the interpercentile range may use temperature values between the first percentile and the ninety-ninth percentile. As noted above, these values may be actual values or calculated from the set of temperature values used to form the temperature distribution. Using one or more non-end-point percentiles may advantageously reduce noise (e.g., the lowest temperature data point may have not adequately communicated with its temperature sensor 26 and therefore, appears much colder than its actual temperature.

As noted above, however, the distribution may simply include actual temperature values or a relatively small set of temperature values that are both actual and calculated. Step 806 therefore may simply select any two of these values to effectively form the interpercentile range without affirmatively calculating the percentiles.

At step 808, the distribution processor 86 compares the interpercentile range temperature value (i.e., a temperature difference) against a prescribed or other threshold value (i.e., another temperature value). That threshold value should be carefully chosen and be consistent with the percentiles selected and other known information (e.g., patient information, modality information, etc.). When using the endpoints of the set of temperature values, for example, the inventors discovered that a threshold value from about 1 to about 4 degrees C. should provide satisfactory results. During testing, the inventors discovered that a value between about 1.4 degrees C. and about 2.8 degrees C. produced even better results.

In illustrative embodiments, if the interpercentile range size is equal to or exceeds the threshold value (or if it simply exceeds the threshold value), then the patient's foot may have a health issue, such as an ulcer or pre-ulcer. During testing, the inventors were surprised to discover that this comparison produced accurate results a significant proportion of the time when using the discussed modalities (e.g., the platforms 16 with the receiving region 17, sensors 26 that actuate as required, etc.). Among other reasons, results of this type can often be dominated by noise producing a high or low end of the range that is well beyond those of the actual end points without the noise. For example, the inventors were concerned that a toe may not sufficiently contact a contact temperature sensor 26, thus appearing cold and producing a much lower low end of the range. They recognized, however, that with closed platforms 16, as well as with open platforms 16, these noise based extremes were less of an issue than originally expected. The platform 16 and its receiving region 17 therefore may obviate these issues.

In fact, the inventors unexpectedly recognized that this comparison also can signal an ischemic condition in the foot 10 that requires treatment. Accordingly, this process may alert a patient and/or caregiver to two potentially common dangerous and life threatening conditions for diabetics— foot ischemia and foot ulcers/pre-ulcers. Accordingly, the range of a set of foot temperature data captures both abnormally warm locations and abnormally cool locations and conveniently presents it as a single statistic that can be easily compared to a threshold.

Alternatively, some embodiments may measure the temperature of a continuous region on the foot. If necessary, this embodiment may exclude the data within a margin from the edges of the foot. After measuring that temperature, this embodiment calculates the range of temperatures within the region and compares the range to a predetermined threshold to determine if the temperature pattern is indicative of some pathology. This alternative embodiments also effectively performs steps 804-808.

The process continues to step 810, which considers whether the foot requires further processing to provide even more accurate results. This may be required in certain applications, or be unnecessary. Some embodiments have a selectable user interface to augment steps 800-808 with one of the below listed processes. Specifically, the method may execute further processes that include one or more of the following (step 812):

Process 1: Simple Comparison Between Locations

In the absence of a contralateral foot for comparison, the temperatures at any two locations on the foot 10 may be compared. For example, the heel may serve as a stable reference point due to its relative temperature stability over time compared to more distal portions of the foot 10.

Variant A: Absolute value above certain threshold.

Measure the temperature at two locations, calculate the absolute value of the difference between the two locations, and compare the difference to a predetermined threshold (e.g., two degrees C.) to determine if the temperature pattern is indicative of some pathology.

Variant B: Asymmetric threshold.

Measure the temperature at two locations on the foot 10. Subtract the temperature a Location 1 from a Location 2 and compare the difference to a Threshold A. Then subtract Location 2 from Location 1 and compare it to Threshold B, where Threshold A is different from Threshold B. Then determine if either of the differences exceed the two different predetermined thresholds. This variant has the advantage of enabling detection of pathologies that result in an abnormally warm region as well as pathologies that may result in an abnormally cool region where the definition of abnormal is dependent on whether the region is warmer or cooler than another region.

Variant C: Unique thresholds for different locations.

Measure the temperature at three locations on the foot 10. Subtract Location 1 from Location 2 and compare it to Threshold A. Then subtract Location 3 from Location 2 and compare it to Threshold B. Then determine if either of the differences exceed the two different predetermined thresholds. This variant enables optimizing accuracy for various anatomical locations. For example, the toes may require a higher threshold than the heel because of the greater temperature variation at more distal regions of the foot 10.

Process 2: Comparison of Locations to a Statistic

Individual locations may be compared to a statistic that summarizes the temperatures over the whole foot 10 instead of relying on a single location for comparison, which may present with unstable temperature patterns over time.

Variant A: Comparison to a central tendency statistic (such as the mean or median).

Measure the temperature over a plurality of discrete locations or over a continuous portion of the foot 10 and use the tendency processor 88 to calculate the mean or median temperature. Measure the temperature of another location either within the region of the average or outside of it. Then subtract the average from the temperature in the location of interest and compare it to a threshold.

Variant B: Comparison to the minimum.

Calculate the minimum temperature among a set of discrete temperature values or from within a continuous portion of the foot 10. If using a continuous portion of the foot 10, the region may exclude the data within a certain margin from the edges of the foot 10. Measure the temperature of another location either within the region of the average or outside of it. Then subtract the minimum from the temperature in the location of interest and compare it to a threshold.

Variant C: Comparison to a percentile.

Similar to Variant B, except instead of calculating the minimum temperature value for comparison, calculate a predetermined percentile, such as the 10th percentile. This approach avoids extremes in the distribution of temperature at the low or the high side, which may result in inaccurate analyses.

Variant D: Comparison with a statistical distribution.

Compute a statistical distribution of the temperatures among a set of discrete temperature values or from within a continuous portion of the foot 10. Measure the temperature of another location either within the region of the average or outside of it. Then determine if the location of interest is within the distribution using common statistical methods.

Process 3: Change Over Time

In some pathologies, the absolute temperature at a given time is not as informative as the change in temperatures over time. Chronic conditions may present as slow changes over a long time and acute conditions may present as fast onset or short-lived patterns.

Variant A: Simple threshold above a baseline.

Illustrative embodiments measure and store the foot temperature at a baseline time reference. Then for a later time t, this embodiment measures the foot temperature again and compares the temperatures at time t with the temperatures at baseline and determines if any location has changed in temperature from the baseline more than a predetermined threshold. Alternatively, this embodiment may measure the difference in temperatures between locations on the foot 10 and compare the spatial differences with the baseline spatial differences. This method has the advantage of personalizing the analysis to an individual's idiosyncratic foot temperature patterns. However, it assumes that the baseline temperatures are a healthy reference location, which may not be true for individuals healing from a recent wound or with other active pathology.

Variant B: Moving average baseline.

In a related embodiment, the baseline temperatures may be calculated as a moving average or a filtered resultant from a time series of multiple sets of temperature data from various locations in time. The average may be taken from a small number of samples to optimize for detecting acute changes in foot temperatures or from a large number of samples to optimize for detecting subtle changes or chronic conditions.

Variant C: Integral of temperature change over time.

In yet another embodiment, the foot temperatures may be compared to a baseline reference or a static threshold for each set of data values in a time series of samples. These comparisons may then be summed, integrated, or otherwise aggregated to generate a summary statistic for the change over time. This approach has an advantage of emphasizing persistent changes over time while filtering out noisy or inconsistent temperature fluctuations.

Variant D: Change in temperature as a response to a stimulus.

In yet another embodiment, the foot's response to a stimulus may be monitored over time. For example, when a foot is placed on a cold or room temperature platform, its response to that exposure over several seconds to several minutes may indicate the vascular health of the foot and the ability of the blood vessels to supply fresh blood to warm the foot. In another example, a foot's thermal response to exercise or other physical activity such as walking may indicate its neurological or vascular health. For example, a foot that becomes abnormally warm during physical activity may lack the physiological mechanisms to thermoregulate.

Process 4: Comparison with Ambient

Comparing foot temperature with ambient temperature provides an opportunity to detect inflammation in the foot 10 in cases where there may be no spatial variation within the foot 10 although the entire foot 10 is inflamed and at elevated temperature.

Variant A: Compare a central tendency statistic to ambient. This embodiment measure the ambient temperature using either background signal from the temperature sensor 26 (e.g., the background of a thermal camera image or non-foot region from a 2D temperature scan) or from a separate temperature sensor 26 that is not measuring foot temperature. This embodiment also measures the temperature across the foot 10 and calculates a central tendency statistic (e.g., mean, median, mode). Next, this embodiment compares the central tendency statistic to the ambient temperature and determines if the difference exceeds a predetermined threshold.

Variant B: Compare a specific location to ambient.

A related embodiment measures ambient temperature, and then measures the foot temperature at a specific location or region on the foot 10. It then compares the temperature at that location to ambient temperature and determines if the difference exceeds a predetermined threshold. This variant has a benefit of allowing the clinician or researcher to select a consistent location on the foot 10 with relatively stable temperatures that is not as susceptible to environmental or other temporary perturbations as other locations.

Variant C: Compare the maximum to ambient.

Another related embodiment measures ambient temperature, and then measures the foot temperatures over the whole foot 10 and calculates the maximum temperature of the foot 10. It then compares the maximum to ambient temperature and determines if the difference exceeds a predetermined threshold. This variant is expected to provide good sensitivity in cases where the warmest portion of the foot 10 may move from scan to scan.

Process 5: Comparison with Body Temperature

This method is similar to Process 4, but less susceptible to intermittent or irregular fluctuations in ambient temperature due to changing environmental conditions. Comparing foot temperature with body temperature may provide a more accurate basis for detecting pathology by accounting for external variables that affect foot temperature.

Variant A: Comparing to internal body temperature.

This embodiment measures internal body temperature either at the core or preferably at the limb closest to the surface measurement location. It then compares the surface foot temperature measurements to the internal body temperature and determine if the difference exceeds a predetermined threshold.

Variant B: limb surface temperature.

This embodiment measures the surface temperature of the limb preferably close to the foot measurement location (e.g., ankle or leg). It then compares the surface foot temperature measurements to the surface limb temperature and determines if the difference exceeds a predetermined threshold. This variant is easier to acquire than internal body temperature as surface temperature sensors 26 may be adhered to the skin to collect surface temperature. This approach has the added benefit of limiting the effects of ambient temperature, physical activity, and vascularity, which would affect the limb as well as the foot 10.

Process 6: Isothermal Area

The size of a region of elevated temperature may be more informative than the specific temperature of that region for certain pathologies, such as monitoring wound healing.

Variant A: Comparing an isothermal area.

This embodiment chooses a comparison from any of the processes described above and calculates the difference between each location in the foot temperature data set and the comparison value. It then determines which locations, pixels, or regions are above a predetermined threshold. Next, it calculates the area of the region that exceeds that threshold in number of points, pixels, or area (e.g., cm2). It determines if the area of elevated temperature exceeds a predetermined threshold.

Variant B: Monitoring isothermal area over time.

This is similar to Method 6, Variant A except that the determination is made as to whether the isothermal area has changed in size over time.

Returning to step 810, if no further processing is necessary, or after completing step 812, the process concludes at step 814, which produces electronic output information, using the output 84, having data relating to the analysis. As discussed above with regard to FIG. 5, this data may be in a form that is readily human understandable and/or storable, or may be in a format that needs further processing. This output information thus may include ulcer information relating to the emergence of an ulcer or pre-ulcer when the percentage of the range size equals or exceeds the threshold value. For example, the output information may have information indicating the presence of a pre-ulcer and the data around the steps performed and the temperature values, ranges, and/or differences, depending on the steps performed. This output information also may have information relating to an ischemic foot condition. The output information alternatively may have information indicating that the foot 10 is healthy and has no maladies (e.g., if the percentage of the range size is less than the threshold value. Indeed, the output information also may have information relating to one or more of the additional processes noted above.

One skilled in the art should recognize that the results may have an accuracy that may be higher or lower depending on the configuration of the system. Thus, although the system may be 90 percent accurate, for example, it is not perfect and may have some false positives and false negatives. The platform 16, base, receiving region 17, sensors 26, etc. can be configured to optimize performance.

By themselves, some of the above noted process options and their variants (including the process of FIG. 8) may detect one distinct type of pathology in the foot 10 and can be optimized to detect that pathology with a high degree of sensitivity and specificity. However, just using one method may not generalize to other types of pathologies. For example, comparing the temperature of the hallux with the heel is beneficial to determine if the hallux may have localized inflammation. However, if the whole foot 10 is inflamed, the temperature difference between those locations will not be significant and may therefore not detect the systemic inflammation. The inventors discovered that combining this with another method, such as comparing the heel temperature with ambient temperature to detect systemic inflammation, may improve the probability of detecting either pathological condition.

Accordingly, although some provide beneficial results alone, illustrative embodiments may combine two or more of noted processes and/or their variants. For example, two or more of those methods may be combined with simple logical terms or in linear combinations to provide a more accurate prediction. For example, some embodiments combine two of the processes, three of the processes, four of the processes, five of the processes, six of the processes, seven of the processes, or one or more of the processes with another process not discussed.

In one embodiment, two or more of the above noted processes are combined with OR statements. For example, if Process 1 is true OR Process 2 is true, then the probability of pathology is high. This combination has the benefit of allowing specialization of the processes to detect certain types of pathologies and naturally increases the sensitivity of the detection system across multiple pathologies. In another embodiment, processes may be combined with AND statements. For example, if Process 1 is true AND Process 2 is true, then the probability of pathology is high. This combination thus may create a highly specific detection process. In another embodiment, processes may be combined as a linear combination of continuous or categorical outputs. For example, if two processes are combined, each which produce a continuous variable output, such as degrees C., the combined formulation may multiply each process variable by a coefficient in order to obtain a final result which may then be used to determine the probability of a pathology. In this embodiment, the formulation may be in the form $R=A*M1+B*M2$ where R is risk, M1 and M2 are Process 1 and Process 2 variables, and A and B are coefficients. This combination technique has the added benefit of weighting the variables unevenly, depending on which is more influential on the pathology the researcher is interested in. Additionally it is optimizable across all of the independent input variables simultaneously to obtain a system which maximizes sensitivity and/or specificity depending on the aims of the researcher.

One skilled in the art will recognize that the optimization of thresholds may be done on a per-process basis or for a set of processes in whatever combinations are used to optimize the sensitivity and specificity of the combined set of processes.

Additionally, instead of applying simple thresholding (either for a single set of foot temperature measurements at one time or for multiple sets of) to identify risk, the magnitude of any of the metrics given in the discussed processes can also be informative of risk. For example, a large difference in the temperature difference described in Process 1 may indicate higher risk than a lower magnitude temperature difference.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product (or in a computer process) for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium.

The medium may be either a tangible medium (e.g., optical or analog communications lines) or a medium implemented with wireless techniques (e.g., WIFI, microwave, infrared or other transmission techniques). The medium also may be a non-transient medium. The series of computer instructions can embody all or part of the functionality previously described herein with respect to the system. The processes described herein are merely exemplary and it is understood that various alternatives, mathematical equivalents, or derivations thereof fall within the scope of the present invention.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the larger network (e.g., the Internet or World Wide Web). Of course, some embodiments of the invention may be implemented as a combination of both software (e.g., a computer program product) and hardware. Still other embodiments of the invention are implemented as entirely hardware, or entirely software.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A foot ulcer detection system comprising:
    a body having a base with a top surface, the top surface of the base having a receiving region configured to receive the bottom of a single foot, the base forming an open platform or a closed platform;
    a set of temperature sensors in communication with the top surface of the receiving region of the open or closed platform, the set of temperature sensors being spaced apart within the receiving region and configured to activate after receipt of a stimulus applied to one or both the open or closed platform and the set of temperature sensors, the set of temperature sensors configured to thermally communicate with the bottom of the single foot within the receiving region to ascertain a current temperature at each of a set of different spaced apart locations of the bottom of the single foot, the set of temperature sensors configured to produce a set of temperature values with each location having one associated temperature value;
    a comparator operatively coupled with the set of temperature sensors, the comparator configured to determine a distribution of temperature values using the set of temperature values, the distribution having an interpercentile range between or including the zero percentile and the one hundred percentile of the set of temperature values, wherein the interpercentile range is a temperature value difference between the temperatures at two different percentiles;
    the comparator further being configured to calculate the interpercentile range and to compare the interpercentile range to a threshold value; and
    an output operatively coupled with the comparator configured to produce ulcer information relating to the emergence of an ulcer or pre-ulcer when the interpercentile range equals or exceeds the threshold value.

2. The foot ulcer detection system as defined by claim 1 wherein the output is coupled with the body.

3. The foot ulcer detection system as defined by claim 1 wherein the ulcer information includes data requiring further processing to indicate the emergence of an ulcer or pre-ulcer.

4. The foot ulcer detection system as defined by claim 1 wherein the output and comparator are spaced from and remote from the body.

5. The foot ulcer detection system as defined by claim 1 wherein the set of temperature values includes a maximum temperature value and a minimum temperature value, the interpercentile range having the minimum temperature value at the zero percentile and the maximum temperature value at the one hundredth percentile.

6. The foot ulcer detection system as defined by claim 1 wherein the interpercentile range has at least one temperature value that is not in the set of temperature values.

7. The foot ulcer detection system as defined by claim 1 wherein the interpercentile range size has a lowest temperature value that is greater than the zero percentile or a highest temperature value that is less than the one hundredth percentile.

8. The foot ulcer detection system as defined by claim 1 wherein the threshold is between 1 degree C. and 4 degrees C.

9. The foot ulcer detection system as defined by claim 8 wherein the threshold is between 1.4 degrees C. and 2.8 degrees C.

10. The foot ulcer detection system as defined by claim 1 wherein the set of different locations comprises between four and one hundred locations that relate to corresponding locations on the bottom of the single foot.

11. The foot ulcer detection system as defined by claim 1 further comprising:
    a second comparator operably coupled with the output, the second comparator configured to determine a central tendency statistic from the set of temperature values, the central tendency statistic being one of mean, median, and mode of the set of temperature values, the second comparator further configured to produce a given value as a function of the central tendency statistic and ambient temperature, and then compare the given value to a second threshold value,
    the output being configured to produce the ulcer information also as a function of the comparison of the given value to the second threshold value.

12. The foot ulcer detection system as defined by claim 11 wherein the second comparator is configured to produce the given value by determining the difference between the central tendency statistic and the ambient temperature.

* * * * *